United States Patent
Grüner et al.

(10) Patent No.: US 9,265,701 B2
(45) Date of Patent: *Feb. 23, 2016

(54) HIGHLY LUSTROUS SILVER-COLORED PIGMENTS WITH HIGH OPACITY AND METALLIC APPEARANCE, PROCESS FOR THE PREPARATION THEREOF AND USE OF SAME

(75) Inventors: Michael Grüner, Auerbach (DE); Thomas Schneider, Lauf a. d. Pegnitz (DE); Günter Kaupp, Neuhaus (DE); Christian Rummer, Nuremberg (DE); Dirk Schumacher, Pegnitz (DE)

(73) Assignee: ECKART GMBH, Hartenstein (DE)

( * ) Notice: Subject to any disclaimer, the term of this patent is extended or adjusted under 35 U.S.C. 154(b) by 226 days.

This patent is subject to a terminal disclaimer.

(21) Appl. No.: 14/007,285

(22) PCT Filed: Mar. 23, 2012

(86) PCT No.: PCT/EP2012/055260
§ 371 (c)(1),
(2), (4) Date: Sep. 24, 2013

(87) PCT Pub. No.: WO2012/130776
PCT Pub. Date: Oct. 4, 2012

(65) Prior Publication Data
US 2014/0010772 A1    Jan. 9, 2014

(30) Foreign Application Priority Data
Mar. 25, 2011    (DE) .......................... 10 2011 001 579

(51) Int. Cl.
*C09C 1/00*    (2006.01)
*A61K 8/19*    (2006.01)
(Continued)

(52) U.S. Cl.
CPC .................. *A61K 8/29* (2013.01); *A61K 8/0254* (2013.01); *A61K 8/19* (2013.01); *A61Q 1/04* (2013.01);
(Continued)

(58) Field of Classification Search
CPC ........ C09D 11/00; C09C 1/00; C09C 1/0015; C09C 1/0021; C01P 2004/51; C01P 2006/65; C01P 2006/66; A61K 8/19; A61K 8/29; A61Q 1/10; A61Q 5/00
USPC .......................... 106/31.6, 418, 438, 415, 439
See application file for complete search history.

(56) References Cited

U.S. PATENT DOCUMENTS

| | | | |
|---|---|---|---|
| 3,923,968 A * | 12/1975 | Basque et al. | ................ 423/611 |
| 4,867,793 A | 9/1989 | Franz et al. | |
| 5,759,255 A * | 6/1998 | Venturini et al. | ............. 106/418 |
| 5,972,098 A | 10/1999 | Andes et al. | |
| 7,413,599 B2 | 8/2008 | Henglein et al. | |

(Continued)

FOREIGN PATENT DOCUMENTS

| | | |
|---|---|---|
| DE | 10331903 A1 | 2/2004 |
| DE | 10320455 A1 | 11/2004 |
| DE | 102008064202 A1 | 6/2010 |
| DE | 102009037935 A1 | 2/2011 |
| DE | 102009049413 A1 | 4/2011 |

(Continued)

OTHER PUBLICATIONS

Technical Data Sheet, Eckart Effect Pigments, Revision 0, Edition Mar. 2011.

(Continued)

*Primary Examiner* — Pegah Parvini
(74) *Attorney, Agent, or Firm* — The Webb Law Firm

(57) ABSTRACT

A silver-colored pigment is provided having a nonmetallic platelet-shaped substrate and at least one ilmenite-containing coating, wherein the nonmetallic platelet-shaped substrate is a nonmetallic platelet-shaped synthetic substrate and the amount of iron compounds, calculated as elemental iron, in the pigment is less than 5.0 % by weight, based on the total weight of the pigment. Processes for preparing the pigment also are provided.

27 Claims, 2 Drawing Sheets

(51) Int. Cl.
| | |
|---|---|
| A61K 8/29 | (2006.01) |
| A61Q 1/10 | (2006.01) |
| A61Q 1/06 | (2006.01) |
| A61Q 3/02 | (2006.01) |
| A61Q 5/06 | (2006.01) |
| A61Q 19/00 | (2006.01) |
| A61Q 19/10 | (2006.01) |
| A61Q 1/04 | (2006.01) |
| A61Q 1/12 | (2006.01) |
| A61K 8/02 | (2006.01) |
| C01B 31/04 | (2006.01) |
| A61Q 5/00 | (2006.01) |

(52) U.S. Cl.
CPC .. *A61Q 1/06* (2013.01); *A61Q 1/10* (2013.01); *A61Q 1/12* (2013.01); *A61Q 3/02* (2013.01); *A61Q 5/06* (2013.01); *A61Q 19/00* (2013.01); *A61Q 19/10* (2013.01); *C01B 31/0423* (2013.01); *C09C 1/0015* (2013.01); *C09C 1/0021* (2013.01); *A61K 2800/436* (2013.01); *C01P 2004/51* (2013.01); *C01P 2006/62* (2013.01); *C01P 2006/63* (2013.01); *C01P 2006/64* (2013.01); *C01P 2006/65* (2013.01); *C01P 2006/66* (2013.01); *C01P 2006/80* (2013.01); *C09C 2200/102* (2013.01); *C09C 2200/202* (2013.01); *C09C 2200/301* (2013.01)

(56) References Cited

U.S. PATENT DOCUMENTS

| | | |
|---|---|---|
| 7,611,574 B2 | 11/2009 | Kniess et al. |
| 2007/0028799 A1* | 2/2007 | Kniess et al. ............... 106/31.6 |
| 2007/0243149 A1 | 10/2007 | Hofacker et al. |
| 2011/0226161 A1 | 9/2011 | Schumacher et al. |
| 2011/0251303 A1 | 10/2011 | Rathschlag et al. |
| 2012/0219607 A1 | 8/2012 | Schmidt et al. |
| 2012/0301521 A1 | 11/2012 | Gruner et al. |

FOREIGN PATENT DOCUMENTS

| | | |
|---|---|---|
| EP | 0246523 A2 | 11/1987 |
| EP | 0289240 A1 | 11/1988 |
| EP | 0681009 B1 | 9/1998 |
| EP | 0723997 B1 | 6/1999 |
| EP | 1682622 A1 | 7/2006 |
| EP | 1980594 B1 | 6/2009 |
| WO | 9743348 A1 | 11/1997 |
| WO | 2004056716 A1 | 7/2004 |
| WO | 2004099319 A2 | 11/2004 |
| WO | 2005063637 A1 | 7/2005 |
| WO | 2007115675 A2 | 10/2007 |

OTHER PUBLICATIONS

Safety Data Sheet according to 1907/2006/EC, Article 31, Eckart Effect Pigments, Printing Date Nov. 14, 2013, pp. 1-6.

Wißling, Peter, Excerpt from "Metallic Effect Pigments Fundamentals and Applications", pp. 24-29.

Byk-Gardner, "Qualitatskontrolle fur Lacke and Kunststoffe", Katalog, 2011/2012, pp. 97-98.

Hepp et al., "Determination of total lead in lipstick: Development and validation of a microwave-assisted digestion, inductively coupled plasma-mass spectrometric method", J. Cosmet. Sci., Jul./Aug. 2009, pp. 405-414, vol. 60.

Maisch, "New effect pigments from grey to black", Progress in Organic Coatings, 1993, pp. 261-272, vol. 22.

Schellenberger et al., "Schmelzvorgang unter der Lupe", Farbe & Lack Publication, Apr. 2007, p. 130 (English-language translation of the relevant part is also attached).

* cited by examiner

HIGHLY LUSTROUS SILVER-COLORED PIGMENTS WITH HIGH OPACITY AND METALLIC APPEARANCE, PROCESS FOR THE PREPARATION THEREOF AND USE OF SAME

CROSS-REFERENCE TO RELATED APPLICATIONS

The present application is the national phase of PCT/EP2012/055260 filed Mar. 23, 2012 and claims priority to German Patent Application No. 10 2011 001 579.5, filed Mar. 25, 2011, the entire disclosures of which are herein incorporated by reference.

BACKGROUND OF THE INVENTION

1. Field of the Invention

The present invention relates to silver-colored pigments comprising nonmetallic platelet-shaped synthetic substrates and at least one ilmenite-containing coating with an amount of iron compounds, calculated as elemental iron, in the pigment of less than 5% by weight, based on the total weight of the pigment, a process for the preparation thereof as well as the use thereof. The invention further relates to an object which is provided with the silver-colored pigments according to the invention as well as a preparation which comprises the latter.

2. Description of Related Art

WO 2004/099319 A2 describes interference pigments with a high covering power, high luster and color change at varying viewing angles, comprising a platelet-shaped substrate and at least one $FeTiO_3$-containing layer. The proportion of $FeTiO_3$ in the layer is 8 to 100% by weight, based on the total weight of the layer. These interference pigments are prepared by the simultaneous deposition of titanium(IV) oxide hydrate and iron(III) oxide hydrate on the substrate surface and subsequent thermal treatment under reducing conditions. A homogeneous distribution of ilmenite inside the coating is thus to be guaranteed.

WO 97/43348 A1 describes unsupported single or multi-coat pearlescent pigments consisting of iron titanate and possibly titanium oxide and/or iron oxide. To prepare these pearlescent pigments, titanium dioxide platelets obtained via a belt process are coated, without intermediate drying, with iron oxide in a wet process, and the resulting pigments are dried and calcined in an oxidizing or reducing gas atmosphere. The pearlescent pigments obtained have a high color strength and exhibit for example a color flop from red to gold or from gold to red. It is also possible to obtain blue-black lustrous pigments.

EP 0 246 523 A2 relates to colored pearlescent pigments, which are for example black-gold, black-red, black-green or dark blue, based on a platelet-shaped substrate which is provided with a compact coating containing iron(II) oxide. The layer containing iron(II) oxide can have a different composition here depending on the preparation process and the substrate used. This invention is aimed at pigments with a high conductivity, which manifests itself in a good shielding from electromagnetic interference fields.

Furthermore, these pigments can be easily aligned in magnetic fields because of their magnetizability.

Commercial ilmenite-coated pearlescent pigments based on natural mica are characterized by R. Maisch in the article, New effect pigments from grey to black, Progress in Organic Coatings, 22 (1993) 261-272.

The use of ilmenite-containing interference pigments, which can be black for example and exhibit strong interference colors at the specular angle, to produce forgeryproof documents and packaging is known from EP 0 681 009 B1.

Many everyday fields can no longer be imagined without silver hues, silver vehicles lend distinction to the streetscape and a silver coloring or varnish gives everyday objects like coffee machines, television sets or packaging a high-class appearance. Metallic effect pigments, in particular aluminum effect pigments, critically determine the silver hue. Regulatory limitations, such as e.g. in the color cosmetics sector, can however limit the field of use of metallic effect pigments. If electromagnetic shielding has a role to play, such as for example in the case of cellular phones, metallic effect pigments are often dispensed with in the varnish, although e.g. aluminum effect pigments, contrary to widespread opinion, are not electrically conductive. If the metallic effect and the visual impression of an aluminum effect pigment are to be preserved in an application, a simple substitution by a silver-colored pearlescent pigment is not possible. Commercial silver-colored pearlescent pigments for example generally do not possess the neutral silver hue that is characteristic of aluminum effect pigments. There is a need, therefore, for pigments that in terms of the optical properties such as, for example, silver hue, opacity, metallic gloss or light/dark flop, come close to metallic effect pigments, yet contain no metal and can thus contribute to the field of use of metallic effect pigments.

The problem on which the present invention was based was that of providing highly lustrous silver-colored pigments which in terms of their visual impression have properties that are characteristic of metallic effect pigments. The silver-colored pigments are not to differ, or to differ only insignificantly, from commercial aluminum effect pigments in their appearance. At the same time, the silver-colored pigments are to be characterized by a high chemicals stability and temperature resistance. The problem on which the invention is based is further that of providing a process for preparing these silver-colored pigments.

SUMMARY OF THE INVENTION

In some non-limiting embodiments, there is provided a silver-colored pigment comprising a nonmetallic platelet-shaped substrate and at least one ilmenite-containing coating, wherein the nonmetallic platelet-shaped substrate is a nonmetallic platelet-shaped synthetic substrate and the amount of iron compounds, calculated as elemental iron, in the pigment is less than 5.0% by weight, based on the total weight of the pigment.

Also provided are preparations, such as coating compositions, and objects, comprising the silver-colored pigment of the present invention.

Also provided are processes for preparing silver-colored pigment comprising:
(i) applying an uncalcined titanium oxide/titanium hydroxide/titanium oxide hydrate layer to a nonmetallic, platelet-shaped, synthetic substrate, (ii) applying an iron oxide/iron hydroxide/iron oxide hydrate layer to the uncalcined titanium oxide/titanium hydroxide/titanium oxide hydrate layer, and (iii) calcining the product obtained in step (ii), under reducing conditions.

BRIEF DESCRIPTION OF THE DRAWINGS

The foregoing summary, as well as the following detailed description, will be better understood when read in conjunction with the appended drawings. In the drawings.

DETAILED DESCRIPTION

Figure 1:
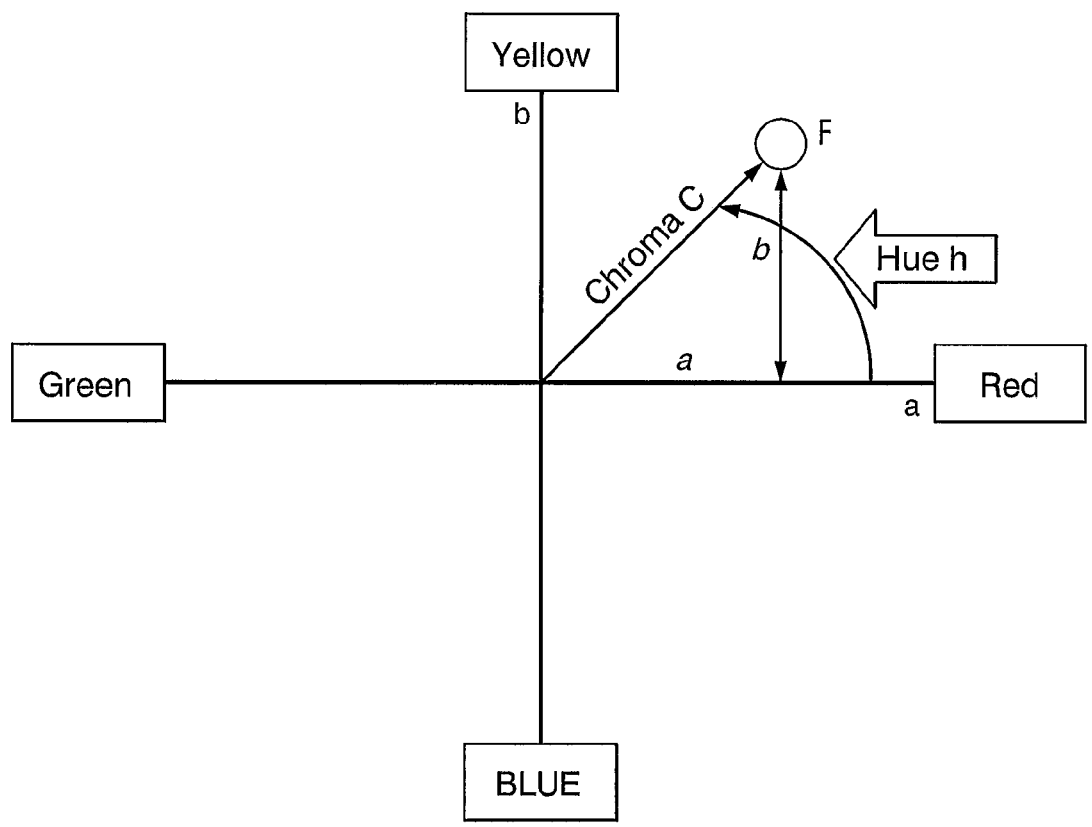
FIG. 1 is a graph of color coordinates in the CIELab color system.

The problem on which the invention is based has been solved through the provision of silver-colored pigment comprising a nonmetallic platelet-shaped substrate and at least one ilmenite-containing coating, wherein the nonmetallic platelet-shaped substrate is a nonmetallic platelet-shaped synthetic substrate and the amount of iron compounds, calculated as elemental iron, in the pigment is less than 5.0% by weight, based on the total weight of the pigment.

The problem on which the invention is based has further been solved through the provision of a process for preparing silver-colored pigment according to one of claims 1 to 11, wherein the process comprises the following steps:
(i) applying an uncalcined titanium oxide/titanium hydroxide/titanium oxide hydrate layer to a nonmetallic, platelet-shaped, synthetic substrate,
(ii) applying an iron oxide/iron hydroxide/iron oxide hydrate layer to the uncalcined titanium oxide/titanium hydroxide/titanium oxide hydrate layer,
(iii) calcining the product obtained in step (ii), under reducing conditions, obtaining the silver-colored pigment.

Preferred developments of the pigment according to the invention are specified in the dependent claims.

Furthermore, a subject of the invention is the use of silver-colored pigment according to the invention in cosmetic formulations, plastics, films, textiles, ceramic materials, glasses and coating compositions, such as paints, printer inks, inks, varnishes and powder coatings.

A further subject of the invention is constituted by preparations that contain the silver-colored pigments according to the invention. Examples of preparations are both coating compositions, such as for example varnishes, powder coatings, paints, printer inks or inks, and cosmetics, plastics, for example plastic granules, etc.

The invention is also aimed at objects which are provided, for example coated, dyed or printed, with silver-colored pigments according to the invention or the preparation of the invention. Thus, coated objects, such as bodyworks, façade elements, coffee machines, mobile telephones, etc., dyed objects such as plastic parts or printed objects, such as paper, cardboard, films, textiles, etc., also form part of the present invention.

According to one preferred variant of the invention, the pigment according to the invention comprises the following structure:
(a) nonmetallic platelet-shaped substrate,
(b) titanium oxide layer,
(c) ilmenite layer,
the pigment being obtainable by
(i) applying an uncalcined titanium oxide/titanium hydroxide/titanium oxide hydrate layer to a nonmetallic, platelet-shaped, synthetic substrate,
(ii) applying an iron oxide/iron hydroxide/iron oxide hydrate layer to the uncalcined titanium oxide/titanium hydroxide/titanium oxide hydrate layer,
(iii) calcining the product obtained in step (ii), under reducing conditions.

After step (iii) the silver-colored pigment according to the invention is obtained.

By titanium oxide/titanium hydroxide/titanium oxide hydrate layer or iron oxide/iron hydroxide/iron oxide hydrate layer is meant, respectively, that a titanium oxide layer and/or titanium hydroxide layer and/or titanium oxide hydrate layer or an iron oxide layer and/or iron hydroxide layer and/or iron oxide hydrate layer may be present.

The amount of iron compounds, calculated as elemental iron, in the silver-colored pigment according to the invention is less than 5.0% by weight, preferably in a range from 1% by weight to 4.3% by weight, particularly preferably in a range from 1.4% by weight to 2.9% by weight and very particularly preferably in a range from 1.5% by weight to 2.3% by weight, based in each case on the total weight of the pigment.

The amount of iron compounds, also referred to below as iron content, is understood in the sense of this invention to mean the complete content of iron compounds with different oxidation numbers in the pigment, the amounts of the entirety of detectable iron compounds being converted arithmetically to elemental iron. This applies not only to the amount of iron compounds in the nonmetallic platelet-shaped synthetic substrates but also to the amount of iron compounds in the coating.

Unless otherwise indicated, the terms "layer" or "coating" are used interchangeably for the purposes of this invention.

The perception of a color as matt, pale or strong is critically dependent on its color saturation, referred to as the chroma or colorfulness. The chroma here is determined by the amount of gray that is present. The higher the gray content, the lower the color saturation.

Considering a point F in the CIELab color system, this point is defined via the three coordinates $L^*$ (lightness), $a^*$ (red-green axis) and $b^*$ (yellow-blue axis). The color coordinates $a^*$ and $b^*$ can also be expressed via polar coordinates $C^*$ (chroma) and $h^*$ (color angle, color locus), the definition being given as follows:

$$C^* = \sqrt{a^{*2} + b^{*2}}$$
$$h^* = \frac{180}{\pi} \cdot \arctan\left(\frac{b^*}{a^*}\right)$$

The chroma therefore corresponds to the length of the vector which points from the origin of the coordinate system to the point F that is to be defined. The lower the value of $C^*$, the closer the point F to the achromatic region of the color coordinate system. The chroma, then, is the distance from the $L^*$ axis or gray axis which stands perpendicularly to the $a^*$, $b^*$ plane (FIG. 1).

The silver-colored pigments according to the invention are notable for low chroma values. With a measurement geometry of 110°, relative to the angle of emergence of the light irradiated at 45°, the chroma is $C^*_{110} \leq 2.4$, preferably in a range from $C^*_{110}=0$ to 2.3, particularly preferably in a range from $C^*_{110}=0.1$ to 2.1 and very particularly preferably in a range from $C^*_{110}=0.2$ to 1.9. With a measurement geometry of 75°, relative to the angle of emergence of the light irradiated at 45°, the chroma is $C^*_{75} \leq 2.4$, preferably in a range from $C^*_{75}=0$ to 2.3, particularly preferably in a range from $C^*_{75}=0.1$ to 2.1 and very particularly preferably in a range from $C^*_{75}=0.2$ to 1.9. The chroma values are measured using the Byk-mac instrument from Byk-Gardner, on the basis of coatings applied to metal panels.

The panel-applied coatings were produced as described below in section IIIa.

The silver-colored pigments according to the invention are further notable for low values, lying close to the coordinate origin, for a* and b* in the CIELab color system. Preferred a* values, measured on the basis of panel-applied coatings using a Byk-mac from Byk-Gardner with the measurement geometries, relative to the angle of emergence of the light irradiated at 45°, of 15°, 25°, 45°, 75° and 110°, are within a range of at most +/−2;

preferred b* values with these measurement geometries are within a range of at most +/−4.

If the pigments according to the invention are subjected to measurement on the basis of powder beds, they are notable even in the unoriented state for low values for a* and b*, and also, consequently, for low chroma values.

The nonmetallic platelet-shaped synthetic substrates of the silver-colored pigments according to the invention are preferably substantially transparent, with preference transparent, i.e. they are at least partly transmissive, preferably transmissive, for visible light.

The nonmetallic platelet-shaped synthetic substrates may be selected from the group consisting of synthetic mica platelets, glass platelets, $SiO_2$ platelets, $Al_2O_3$ platelets, synthetic boehmite platelets, polymer platelets, synthetic platelet-shaped substrates which comprise an inorganic-organic hybrid layer, and mixtures thereof. The nonmetallic platelet-shaped synthetic substrates are preferably selected from the group consisting of synthetic mica platelets, glass platelets, $Al_2O_3$ platelets and mixtures thereof. Particularly preferably the nonmetallic platelet-shaped synthetic substrates are selected from the group consisting of synthetic mica platelets, glass platelets and mixtures thereof. Synthetic mica platelets are a particularly preferred substrate.

Unlike nonmetallic platelet-shaped synthetic substrates, platelet-shaped natural substrates possess the drawback of possibly containing impurities due to intercalated extraneous ions. These impurities may alter the hue and/or reduce the lightness L*. Typical impurities in natural mica, for example, include nickel, chromium, copper, iron, manganese, lead, cadmium, arsenic and/or antimony and/or compounds thereof, which may give the natural mica, for example, a coloration.

The amount of the aforementioned extraneous ions, with the exception of iron, calculated as elemental metal, in the nonmetallic platelet-shaped synthetic substrate is preferably in each case less than 15 ppm, more preferably less than 10 ppm, based in each case on the total weight of the substrate.

The iron content, calculated as elemental iron, of the nonmetallic platelet-shaped synthetic substrates ought in particular to be as low as possible and ought preferably to be less than 0.20% by weight, preferably in a range from 0.01% by weight to 0.20% by weight, with further preference in a range from 0.03% by weight to 0.19% by weight and with particular preference in a range from 0.04% by weight to 0.18% by weight, based in each case on the total weight of the substrate.

The iron content of the nonmetallic platelet-shaped synthetic substrates is determined preferably via X-ray fluorescence (XRF) analysis. For such analysis, the nonmetallic platelet-shaped synthetic substrates are admixed with lithium tetraborate, melted in an oxidizing atmosphere and subjected to measurement in the form of a homogeneous glass tablet. The instrument used as measuring instrument was the Advantix ARL from Thermo Scientific.

As well as the color neutrality of the nonmetallic platelet-shaped synthetic substrate, its lightness also shares responsibility for the visual impression given by pigments based thereon. The lightness L* of the nonmetallic platelet-shaped synthetic substrates, determined by diffuse color measurement of the respective powder beds using a CR 310 colorimeter from Konica Minolta, is preferably ≥90, particularly preferably ≥92 and very particularly preferably ≥95.

A further difference between nonmetallic platelet-shaped natural and synthetic substrates is that as a result of their production the surface of platelet-shaped natural substrates is not ideally smooth but may instead have irregularities, such as steps, for example. Nonmetallic platelet-shaped synthetic substrates generally have smooth surfaces and also a uniform thickness within one individual substrate particle and also, preferably, over the entirety of all of the substrate particles. The surface therefore affords only few scattering centers for incident and reflected light, and consequently, after these platelet-shaped substrates have been coated, allows pigments which are more glossy than those with, for example, platelet-shaped natural mica as their substrate.

Furthermore, contaminations due to heavy metals, particularly in cosmetic formulations, are unwanted in the interest of the consumer. Elevated levels of lead in cosmetic formulations, in particular, are unwanted. Color additives are monitored by the FDA for their lead content and must not exceed a limiting value of 20 µg/g. Other cosmetic ingredients are subject to the responsibility of the manufacturers with regard to their lead content (Nancy M. Hepp, William R. Mindak, John Cheng, J. Cosmet. Sci., 60, 405-414 (July/August 2009)).

In one embodiment the lead content of the synthetic mica platelets which can be used as substrate is preferably less than 5 ppm, with preference in a range from 0.05 ppm to 3 ppm and particularly preferably in a range from 0.03 ppm to 2 ppm. Most preferably the synthetic mica platelets contain no lead and no lead compounds.

In another embodiment, the silver-colored pigments according to the invention based on synthetic mica platelets have a total lead content of preferably less than 10 ppm, with preference from a range from 0.0 ppm to less than 9 ppm, with further preference from a range from 0.0 ppm to less than 8 ppm, still more preferably from a range from 0.1 ppm to less than 7 ppm, and particularly preferably from a range from 0.1 ppm to less than 6.5 ppm.

The lead content of the synthetic mica platelets and also of the silver-colored pigments based thereon is determined in this context via solids graphite tube atomic absorption spectrometry. The instrument used is preferably a ZEENIT 650 with SSA 600 solids sampler from Analytik Jena.

In another embodiment, the nonmetallic platelet-shaped synthetic substrates may have a refractive index from a range from 1.55 to 1.70, preferably from a range from 1.58 to 1.68 and particularly preferably from a range from 1.59 to 1.65.

Where the nonmetallic platelet-shaped synthetic substrate consists of glass platelets, preference is given in the context of this invention to using those which are produced in accordance with the processes described in EP 0 289 240 A1, WO 2004/056716 A1 and WO 2005/063637 A1. The glass platelets which can be used as substrate may have a composition, for example, in accordance with the teaching of EP 1 980 594 B1.

Where the nonmetallic platelet-shaped synthetic substrate consists of synthetic mica, this mica may have various chemical compositions and may differ in its optical properties among others. Differences in the platelet-shaped substrate may also be apparent in the pigment based thereon. The choice of suitable synthetic platelet-shaped mica as the substrate for coating is therefore highly important for the visual appearance of the resulting pigments.

Synthetic mica platelets as substrate are preferably, in the context of this invention, fluorophlogopite of the general formula $X_1Y_{2-3}n(Z_4O_{10})F_2$, where X may be selected from the group consisting of $K^+$, $Na^+$, $Li^+$ and/or $Ca^{2+}$, Y may be selected from the group consisting of $Mg^{2+}$ and/or $Zn^{2+}$, and Z may be selected from the group consisting of $Si^{4+}$ and/or $Al^{3+}$, and n is ½ or 1. It is particularly preferred to use fluorophlogopite of the formula $KMg_3AlSi_3O_{10}F_2$, $KMg_2½(Si_4O_{10})F_2$ or $NaMg_2½(Si_4O_{10})F_2$ as nonmetallic platelet-shaped substrate. Very particularly preferred here is fluorophlogopite of the formula $KMg_3AlSi_3O_{10}F_2$.

Platelet-shaped fluorophlogopite is a substrate with high temperature stability and with chemicals stability, and is extremely suitable for the purposes of the present invention.

The production of the synthetic mica can be tailored, with the consequence that the resultant synthetic mica platelets have as few defects as possible.

The synthetic mica platelets used with preference as nonmetallic platelet-shaped synthetic substrate preferably comprise, according to X-ray fluorescence analysis, the constituents mentioned in Table 1, in the ranges listed.

TABLE 1

Preferred compositions of platelet-shaped synthetic mica according to X-ray fluorescence (XRF) analysis
Composition of synthetic mica platelets, FIGURES in % by weight, based in each case on the total weight of the synthetic mica platelets

| | |
|---|---|
| $SiO_2$ | 38 to 46 |
| $Al_2O_3$ | 10 to 14 |
| $K_2O$ | 9 to 13 |
| $Fe_2O_3$ | 0.01 to 0.25 |
| MgO | 26 to 34 |
| MnO | 0 to 0.05 |
| $Na_2O$ | 0 to 13 |

Even in the event of minor deviations from the figures given by way of example in Table 1, it is possible to obtain the silver-colored pigments according to the invention. It is self-evident that the fraction of coloring components here ought not to deviate significantly from the figures given in Table 1, and that no other coloring components, or only insubstantial traces of coloring components, may be present in the substrate.

Preferred magnesium oxide values for the silver-colored pigments according to the invention according to X-ray fluorescence analysis are situated in a range from 10% to 30% by weight, particularly preferably in a range from 13% to 27% by weight, very particularly preferably in a range from 17% to 23% by weight, based in each case on the total weight of the pigments.

Applied to the nonmetallic platelet-shaped synthetic substrates is at least one high-index layer having a refractive index of n>2.0, preferably of n>2.2. The at least one high-index layer has a metal oxide layer and/or a metal hydroxide layer and/or a metal oxide hydrate layer or consists thereof.

For the formation of an ilmenite layer, the nonmetallic platelet-shaped synthetic substrate must comprise not only at least one titanium oxide layer but also at least one adjacent iron oxide layer and/or at least one titanium hydroxide layer and at least one adjacent iron hydroxide layer and/or at least one titanium oxide hydrate layer and at least one adjacent iron oxide hydrate layer. Under reducing conditions, preferably in the presence of forming gas ($N_2/H_2$), and at temperatures of at least 500° C., the reaction to form ilmenite takes place at the interface between titanium oxide layer and iron oxide layer or between titanium oxide hydrate layer and iron oxide hydrate layer or between titanium hydroxide layer and iron hydroxide layer. In the boundary region there is a partial penetration of both layers, and ilmenite is formed. In the resultant silver-colored pigments according to the invention, accordingly, a gradient is found from a layer consisting exclusively of titanium oxide to a layer consisting exclusively of ilmenite. In the layer which after subsequent calcining comprises titanium oxide, there may additionally be small amounts of titanium suboxide species that are formed under the reducing conditions, the fraction thereof being sufficiently small as not to affect the appearance of the silver-colored pigments according to the invention.

In accordance with one preferred embodiment of the invention, the fraction of titanium oxide in the coating decreases from the substrate-facing side to the substrate-remote side of the titanium oxide layer. Accordingly, the ilmenite layer also has a concentration gradient which decreases in the substrate direction.

In order to obtain the silver-colored pigments according to the invention, the titanium dioxide needed for formation of ilmenite may be present in the anatase or rutile form. In one preferred embodiment, the titanium dioxide is in the rutile form. The rutile form may be obtained by applying a layer of tin dioxide to the platelet-shaped transparent substrate that is to be coated, before the titanium dioxide layer is applied, for example. Titanium dioxide in the rutile modification crystallizes on this layer of tin dioxide. The tin dioxide here may take the form of a separate layer, in which case the layer thickness may amount to a few nanometers, for example less than 10 nm, more preferably less than 5 nm, still more preferably less than 3 nm.

In one particularly preferred embodiment, the reaction to form ilmenite takes place at the interface of the titanium oxide hydrate/titanium hydroxide layer and iron oxide hydrate/iron hydroxide layer; in other words, a pigment coated with titanium oxide hydrate and/or with titanium hydroxide is coated with iron oxide hydrate and/or iron hydroxide, without prior calcining and without prior optional isolation, and is subsequently treated or calcined at elevated temperature under reducing conditions.

The silver-colored pigments according to the invention are notable for a neutral or pure silver hue without color tinge, for example without a weakly blue, greenish, reddish or golden coloration, which might give a visual suggestion of a pearlescent pigment. Neutral or pure silver hues are characteristic of metallic effect pigments, such as aluminum effect pigments, for example. The silver-colored pigments according to the invention are therefore devoid of the incidence of interference color and complementary color, which is characteristic of pearlescent pigments and which occurs particularly on a white substrate, depending on the viewing angle. The silver-colored pigments according to the invention also lack the depth gloss typical of pearlescent pigments.

If the ilmenite-forming reaction is incomplete, and hence iron(III) oxide is still present after the reduction, then the resulting pigments possess a brownish coloration. This deviation from a neutral silver hue can be seen with the naked eye. In one preferred embodiment, the silver-colored pigments according to the invention have an iron(III) oxide content of less than 0.5% by weight, more preferably from a range from 0.0% by weight to 0.4% by weight, still more preferably of less than 0.3% by weight, with particular preference from a range from 0.1% by weight to 0.3% by weight, based in each case on the total weight of the pigment.

Because of the ilmenite layer, typical properties of pearlescent pigments such as depth gloss and transparency are lost. Instead, the silver-colored pigments according to the invention have characteristic features of metallic effect pigments, such as the outstanding opacity.

Comparing the silver-colored pigments according to the invention with silver-colored pearlescent pigments without an limonite layer in terms of their optical properties, it is found that the silver-colored pigments according to the invention, even when the ilmenite content is very low, evoke the visual impression of an aluminum effect pigment. The transparency which is present in pearlescent pigments without an ilmenite layer gives way, with pigments having an ilmenite layer, to the opacity characteristic of metallic effect pigments, and the soft gloss, which appears to come from deep down, is replaced by the hard metallic luster.

The light/dark flop as well that characterizes metallic effect pigments and is particularly pronounced for aluminum effect pigments can be observed to an increased extent in the silver-colored, ilmenite-coated pigments according to the invention. It is therefore preferred for the pigments according to the invention to be not transparent and to have preferably a metallic light/dark flop.

Since the pigments according to the invention have a metallic appearance by virtue of the ilmenite layer, and yet neither a metallic core nor a metallic layer is present on the nonmetallic platelet-shaped synthetic substrate, the outstanding chemicals stability and the high temperature stability that characterize pearlescent pigments are retained. Of course, chemically stable and temperature-stable metallic effect pigments are available commercially as well, but in contrast to pearlescent pigments they must be subjected to an elaborate aftertreatment in order to attain these stability qualities.

The inventors have surprisingly found a new pigment category which in terms of chemical and mechanical stability is similar to the pearlescent pigments, but in terms of its optical properties is remarkably similar to metallic effect pigments.

The silver-colored pigments according to the invention have proven extremely temperature-stable and also corrosion-stable and chemically stable.

The silver-colored pigments according to the invention are suitable in particular for uses in which the requirements for corrosion resistance of the pigment are very high. They are suitable for example in the painting of automobile accessories as well as wheel rim coatings, which are exposed e.g. to spray/salt water. The pigments according to the invention are also eminently suitable for the painting of facade elements, which are exposed to constant weathering.

The chemicals stability of the silver-colored pigments according to the invention is verified on the basis of coatings applied to metal panels and exposed to the action of an acid or alkali.

The corrosion resistance of the silver-colored pigments according to the invention was determined on the basis of its gassing behavior in an aqueous carbomer gel system. Whether the silver-colored pigments according to the invention possess the desired temperature stability is determined by storage of the pigments at temperatures of 100° C. to 200° C. Following storage, the pigments are investigated for possible color changes by means of doctor-blade drawdowns.

The color-neutral, silver-colored pigments according to the invention with metallic appearance can be obtained, on the basis of nonmetallic platelet-shaped synthetic substrates having above-identified properties, surprisingly even in the presence of a very thin ilmenite layer, having an average layer thickness from a range from 1 to 20 nm, preferably 6 to 15 nm. Surprisingly, the formation of a thicker ilmenite layer is unnecessary. Hence the formation of a very thin itmenite layer at less than 20 nm is sufficient to give a silver-colored pigment according to the invention which is similar in its optical properties to a metallic effect pigment, in particular to an aluminum effect pigment.

In the absence of iron components in addition to those necessary for ilmenite formation, an iron/titanium weight ratio, calculated as the ratio of elemental iron to elemental titanium, from a range from 0.1 to 0.25 may be sufficient in order to suppress the characteristic pearlescence. Following ilmenite coating, the silver-colored pigments are identical in their optical properties to metallic effect pigments, while functional properties of pearlescent pigments are retained. Accordingly, the silver-colored pigments of the present invention can be employed ideally in applications in which a metallic appearance is desired but a metallic effect pigment is not.

An iron/titanium weight ratio, calculated as the ratio of elemental iron to elemental titanium, of less than 0.1 would impair the opacity of silver-colored pigments, while an iron/titanium weight ratio of more than 0.25 makes virtually no additional contribution to the opacity.

For the purpose of determining the iron/titanium weight ratio, the titanium oxide content as determined by X-ray fluorescence measurements is converted arithmetically to elemental titanium. The amount of iron compounds is likewise converted arithmetically to elemental iron. As already mentioned when defining the iron content, the titanium content also describes the entirety of all of the detectable titanium compounds in the pigment, converted arithmetically to elemental titanium.

The iron/titanium weight ratio of the silver-colored pigments according to the invention is dependent on the particle size of the pigment and/or on the average thickness of the nonmetallic platelet-shaped synthetic substrate. Both the iron content and the titanium content are therefore dependent on the average particle size $D_{50}$ and on the average thickness of the nonmetallic platelet-shaped synthetic substrates to be coated. The optical layer thickness of the layer surrounding the platelet-shaped nonmetallic synthetic substrate is responsible for the color of the resulting pigments.

A coating with titanium dioxide with an optical layer thickness of 140 nm, for example, produces silver-colored pearlescent pigments. However, the amount of, for example, titanium dioxide that is necessary for achieving this optical layer thickness is dependent on the average particle size $D_{50}$ and average thickness of the nonmetallic platelet-shaped substrates to be coated. A silver-colored pearlescent pigment based on natural mica and having an average particle size $D_{50}$ of approximately 20 μm (e.g. Phoenix 1001, from Eckart) has a titanium dioxide content of approximately 30% by weight, while a corresponding pearlescent pigment with an average particle size $D_{50}$ of approximately 10 μm (e.g. Phoenix 2001, from Eckart) has a titanium dioxide content of approximately 37% by weight.

In order to define, for the silver-colored pigments according to the invention, an iron/titanium weight ratio which is independent of the average particle size $D_{50}$ and/or average thickness of the nonmetallic platelet-shaped synthetic substrate, the fraction of the coating is taken into account when determining the iron/titanium weight ratio, in accordance with Formula (I):

$$\frac{\text{Iron content (\% by weight)}}{\text{Titanium content (\% by weight)}} \cdot \text{Fraction of the coating (\% by weight)}. \qquad (I)$$

The fraction of the coating (% by weight) is defined from the total weight of the pigment minus the fraction of the substrate (% by weight). The iron content is defined as the entirety of all of the detectable iron compounds in the pigment, converted arithmetically to elemental iron. Similarly, the titanium content is defined as the entirety of all of the detectable titanium compounds in the pigment, converted arithmetically to elemental titanium.

The iron/titanium weight ratio in accordance with Formula (I) for the silver-colored pigments according to the invention is situated preferably in a range from 1 to 8, with preference in a range from 2 to 7.5, particularly preferably in a range from 2.5 to 7, and very particularly preferably in a range from 3 to 6.

The opacity of the silver-colored pigments according to the invention was determined on the basis of the lightness values L*, measured using the Byk-mac instrument from Byk-Gardner, of coatings applied to black-white opacity charts (Byko-Chart 2853, Byk-Gardner). For this purpose, the lightness values on the black and white background of the black-white opacity chart were determined with a measurement geometry of 110°, relative to the angle of emergence of the light irradiated at 45°, and the ratio thereof was formed. In the context of this invention, values from $L^*_{110, black}/L^*_{110, white}$ of more than 0.5 are considered to be opaque.

The opacity of the silver-colored pigments according to the invention is additionally dependent on their overall thickness. The thicker the substrate of the silver-colored pigments according to the invention, the lower their opacity. For example, silver-colored pigments according to the invention which are based on glass platelets having a thickness of more than 1 μm give a lower opacity than silver-colored pigments according to the invention which possess as substrate plateletshaped synthetic mica having a thickness of 400 nm. This can be explained by the fact that in a defined amount of pigment, of 1 g pigment, for example, the number of individual pigments in the case of thinner pigments is of course greater than would be the case for thicker pigments. This smaller pigment count is responsible, in an application, for a comparatively lower opacity.

In contrast to transparent pearlescent pigments, opaque metallic effect pigments are notable for a higher covering power. The covering power of the silver-colored pigments according to the invention is comparable with that of metallic effect pigments, in particular aluminum effect pigments.

At the specular angle, metallic effect pigments exhibit the typical metallic luster, which is lost outside the specular angle. Outside the specular angle, applications containing metallic effect pigments appear less glossy and dark. This effect is also observed with the silver-colored pigments according to the invention.

Following application to, for example, a metal panel, and drying, a coating material which contains the silver-colored pigments according to the invention exhibits a substantially angle-dependent gloss effect or what is called a light/dark flop. This change in lightness is described by the flop index. The flop index is defined in accordance with Alman as follows (S. Schellenberger, M. Entenmann, A. Hennemann, P. Thometzek, Farbe and Lack, 04/2007, p. 130):

$$\text{Flop index} = 2.69 \cdot (L_{E1} - L_{E3})^{1.11}/L_{E2}^{0.86}$$

where $L_{E1}$ is the lightness of the near-specular measuring angle (E1=15° relative to the specular angle), $L_{E2}$ is the lightness of the measuring angle between near-specular and far-specular angle (E2=45° relative to the specular angle) and $L_{E3}$ is the lightness of the far-specular measuring angle (E3=110° relative to the specular angle). The larger the numerical value of the flop index, the more greatly the light/dark flop is expressed.

Given a comparable particle size distribution and in particular given a comparable average particle size $D_{50}$, the flop index of the silver-colored pigments according to the invention is virtually identical to that of an aluminum effect pigment.

The ratio of flop index to $D_{50}$ describes the angle-dependent change in lightness of the silver-colored pigments according to the invention as a function of the average particle size $D_{50}$ of the respective pigment. The flop index/$D_{50}$ ratio is situated preferably in a range from 0.5 to 1.9, particularly preferably in a range from 0.6 to 1.8 and very particularly preferably in a range from 0.7 to 1.7.

The visual appearance of the pigments according to the invention cannot be reproduced by simple mixing of a conventional silver-colored pearlescent pigment with diverse dyes/pigments such as carbon black, for example. If opaque dyes/pigments are used, the gloss and the effect of the silver-colored pearlescent pigment are lost. When transparent dyes/pigments are used, therefore, it is impossible to achieve opacity.

When applied coatings which contain the silver-colored pigments according to the invention are compared with applied coatings which contain silver-colored pigments not according to the invention, the different visual impression is immediately evident to a viewer.

Applied coatings which contain exclusively the silver-colored pigments according to the invention produce a visual impression of pure or color-neutral silver, i.e. without additional color impressions. Furthermore, these applied coatings exhibit a metallic appearance and an extraordinary glitter effect.

Figure 2:
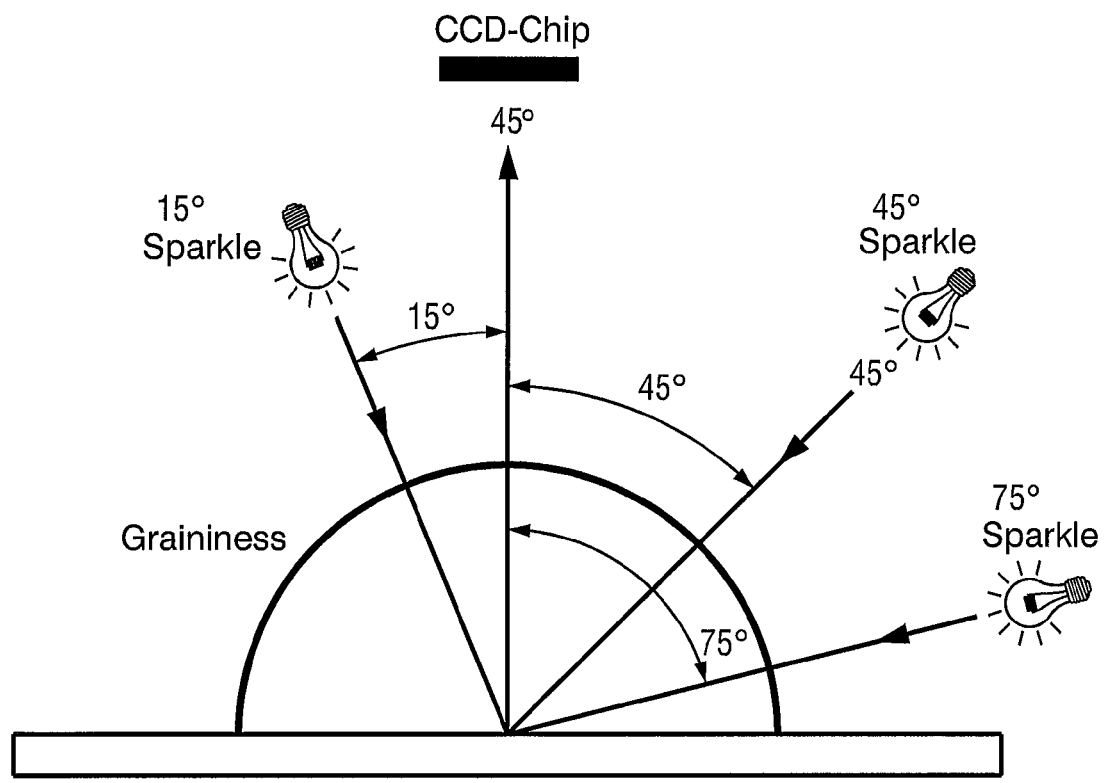
FIG. 2 is a diagram of Byk mac effect measurement geometries (Byk-Gardner, catalog "Qualitatskontrolle f t ir Lacke and Kunststoffe [Quality Control for coatings and plastics]" 2011/2012, p. 97).

In order to describe objectively the optical effect of the silver-colored pigments according to the invention, multiangle color measurements and effect measurements were carried out using a BYK-mac (Byk-Gardner) on the basis of coatings applied to metal panels. The BYK-mac measures the total color impression at different viewing angles and light conditions. The multiangle color measurement serves here to capture and describe the light/dark flop and/or color flop of coating materials provided with effect pigments. The measurement geometries (−15°), +15°, 25°, 45°, 75°, 110° are measured relative to the angle of emergence of the light irradiated at 45°. To simulate effect changes upon direct and diffuse illumination, glitter effect and graininess are simultaneously monitored with the help of a high-resolution CCD camera. The glitter effect, caused by the reflecting ability of the individual effect pigments, is only perceived upon direct solar irradiation, and changes depending on the illumination angle. For this reason, the Byk-mac illuminates the sample with very bright LEDs at three different angles (15°/45°/75°, FIG. 2). The CCD camera takes an image perpendicularly to the surface in each case. The images are analyzed using image processing algorithms, using the histogram of the lightness stages as a basis for calculating the glitter parameters. In order to ensure better differentiation, the glitter effect can be described by a two-dimensional system, the glitter area S_a and the glitter intensity S_i, which can also be summarized in a one-dimensional value, the glitter degree S_G (Byk-Gardner, catalog "Qualitatskontrolle für Lacke and Kunststoffe" [Quality control for coatings and plastics] 2011/2012, pp. 97/98).

The measured glitter area and glitter intensity is influenced by the orientation of the pigments. A pigment with good alignment, in other words aligned largely plane-parallel to the substrate, has the highest measurement values at an illumination geometry of 15°, in a comparison of the glitter measurement values S_a, S_i and S_G obtained in the illumination geometries 15°, 45° and 75°, since a large part of the pigments directly reflects the irradiated light. With an illumination geometry of 45°, the irradiated light is largely reflected directly and is thus perceived as a relatively weak glitter effect when observed perpendicularly to the application. The glitter effect observed with this illumination geometry is attributable partly to pigments with incorrect orientation, i.e. without plane-parallel orientation, which are able to divert the light irradiated at 45° in the direction of the detector. With an illumination geometry of 75°, no glitter effect, or only a weak glitter effect, is perceived perpendicularly to the application. This effect is in turn caused by incorrectly arranged pigments.

Consequently, a well-oriented pigment has the greatest glitter effect at 15°; the minimum glitter effect, relative to the 15° measurement, is observed at 75°. In the case of a poorly oriented pigment, the differences of the measurement values observed at 15°, 45° and 75° illumination geometry are smaller, since light is always reflected in the direction of the detector as a result of the incorrect orientation.

The one-dimensional glitter degree S_G is critical to the visual impression. The higher the numerical value of S_G, the higher the glitter effect that can be perceived by the eye. In a two-dimensional representation, the glitter degree S_G can be divided into the components of glitter intensity S_i and glitter area S_a. Since both components have a critical influence on the glitter degree S_G, it may be the case that a pigment in the measurement geometries 15°, 45° and 75° exhibits virtually the same glitter degree S_G, despite the fact that the numerical values of S_a and S_G at the angles considered increase or decrease significantly.

In contrast to silver-colored pearlescent pigments based, for example, on natural mica, which are different neither in layer construction nor in particle size from the silver-colored pigments according to the invention, these silver-colored pigments according to the invention, at a measurement geometry of 15°, exhibit far higher values for glitter intensity S_i and glitter area S_a. Accordingly, the visual difference that is visible for a viewer can also be demonstrated by measurement.

With an average particle size $D_{50}$ of the pigments according to the invention from a range from 15 to 25 µm, the glitter intensity S_i with a measurement geometry of 15°, relative to the angle of emergence of the light irradiated at 45°, is preferably >10, particularly preferably >11 and very particularly preferably >12. With an average particle size $D_{50}$ of the pigments according to the invention from a range from 5 to <15 µm, the glitter intensity S_i with a measurement geometry of 15°, relative to the angle of emergence of the light irradiated at 45°, is preferably >5, particularly preferably >6 and very particularly preferably >7.

As well as the glitter intensity S_i, the flop index, as already mentioned, is also dependent on the average particle size $D_{50}$. A change in the average particle size $D_{50}$ has consequences to a particular degree for these two numerical characteristics. The product of flop index and glitter intensity S_i as a function of the average particle size $D_{50}$, in accordance with Formula (II)

$$\text{Flop intensity } (F_i) = \frac{\text{Flop index} \cdot \text{S\_i}}{D_{50}} \quad \text{(II)}$$

is defined as flop intensity ($F_i$) and impressively demonstrates the visible difference between the silver-colored pigments according to the invention and pigments that are available commercially. The value for the product of flop index and glitter intensity as a function of the average particle size $D_{50}$, in accordance with Formula (II), is preferably at least 10. The higher this value, the more glittery and metallic the pigment appears to a viewer.

For the preparation of the silver-colored pigments according to the invention, the nonmetallic platelet-shaped synthetic substrate is preferably suspended in water. To the suspension is added, preferably at a temperature from a range from 50° C. to 100° C. and preferably at a pH which is held constant and which comes from a range from 1.4 to 4.0, preferably a water-soluble inorganic tin compound and then preferably a water-soluble inorganic titanium compound. When the addition of the water-soluble titanium compound is at an end, the suspension then obtained is preferably stirred for at least 30 minutes, and then preferably a water-soluble inorganic iron compound is added. After the end of the reaction, the nonmetallic platelet-shaped synthetic substrate, which is now covered with a titanium oxide hydrate/titanium hydroxide layer and with an iron oxide hydrate/iron hydroxide layer, is separated off, washed if desired, optionally dried and subjected preferably at temperatures in the range from 500° C. to 1200° C. under reducing conditions, particularly preferably in the presence of forming gas ($N_2/H_2$) to thermal treatment or calcining. The thermal treatment or calcining is carried out preferably until the iron oxide hydrate/iron hydroxide present has undergone virtually complete, preferably complete, reaction to form ilmenite.

According to WO 2004/099319 A2, it is extremely important that in the preparation of ilmenite-containing pigments, the water-soluble inorganic titanium compound and the water-soluble inorganic iron compound are applied simultaneously to a platelet-shaped substrate which may have already been coated. It is additionally noted that the simultaneous addition of both components allows pigments to be obtained that have optical properties improved relative to the prior art.

In the context of this invention, however, it has surprisingly been found that when nonmetallic platelet-shaped synthetic substrates are used, even in the case of successive addition, as known from the prior art, of the water-soluble inorganic titanium compound and iron compound, it is possible to obtain highly lustrous silver-colored pigments with a high glitter intensity, a pronounced light/dark flop, and a high covering power, which do not have the disadvantages referred to in WO 2004/099319 A2.

It has further proven exceptionally advantageous, in contrast to EP 0 246 523 A2, for example, to add the water-soluble inorganic iron compound in situ and not to use as starting material a pearlescent pigment which is coated with titanium dioxide and has already been calcined. Given identical layer construction, consisting for example of a titanium dioxide layer and an ilmenite-containing layer, the difference in process between calcining prior to application of the water-soluble inorganic iron compound and continuing the coating operation in situ is manifested in the chemicals stability. The silver-colored pigments according to the invention which are produced without prior calcining are significantly more stable toward acid and alkali than pearlescent pigments produced in accordance with EP 0 246 523 A2, starting from a calcined pigment. The silver-colored pigments according to the invention are also superior in chemicals stability to pearlescent pigments obtained by simultaneous addition of a water-soluble inorganic titanium compound and a water-soluble inorganic iron compound. The application of the iron oxide hydrate/iron hydroxide layer to the uncalcined or unannealed titanium oxide hydrate/titanium hydroxide layer is essential for the structural difference of the pigments according to the invention relative to the pearlescent pigments known from the prior art. The inventors assume that when uncalcined titanium oxide hydrate/titanium hydroxide layers are used, the iron oxide hydrate/iron hydroxide layer that is applied subsequently is able to penetrate to a greater extent into the pores of the adjacent titanium oxide hydrate/titanium hydroxide layer. This improved penetration produces a virtually complete conversion to limonite, not only directly at the interface.

When pearlescent pigments which have already been calcined and are covered with titanium dioxide are used, such penetration is not possible. Moreover, calcined titanium dioxide is much slower to react than titanium oxide hydrate or titanium hydroxide. Even at low layer thicknesses, therefore, the conversion to ilmenite is usually incomplete. This is manifested particularly in a poorer chemicals stability.

The silver-colored pigments according to the invention are not multilayer pearlescent pigments whose layer construction comprises a high-index, low-index, high-index coating.

For emulating the optical properties of an aluminum effect pigment, the nonmetallic platelet-shaped synthetic substrate ought preferably to have properties as follows. In the case of one preferred variant of the invention, the nonmetallic platelet-shaped synthetic substrate meets all of the properties set out hereinbelow in relation to extraneous-ion content, substrate thickness, and lightness.

In order, besides the perceived silvery color in the pigments according to the invention, to avoid a color tinge or coloration, the nonmetallic platelet-shaped synthetic substrate ought to have only negligible quantities of intercalated extraneous ions which may alter the hue. The nonmetallic platelet-shaped synthetic substrate is preferably substantially colorless, preferably colorless.

The silver-colored pigments according to the invention are preferably nonmagnetic or only slightly magnetic. Furthermore, the silver-colored pigments according to the invention are not electrically conductive.

The average thickness of the substrate is preferably selected such that the pigments according to the invention have a high opacity. The average thickness of the nonmetallic platelet-shaped synthetic substrates to be coated is situated preferably in a range from 50 nm to 5000 nm, with preference in a range from 60 nm to 3000 nm, and particularly preferably in a range from 70 nm to 2000 nm.

In one embodiment, the average thickness for glass platelets as the substrate to be coated is situated preferably in a range from 750 nm to 1500 nm. Glass platelets of this kind are available commercially on a broad basis. Further advantages are offered by thinner glass platelets. Thinner substrates lead to a lower overall layer thickness of the silver-colored pigments according to the invention. Accordingly, preference is likewise given to glass platelets whose average thickness is situated in a range from 100 nm to 700 nm, more preferably in a range from 150 nm to 600 nm, particularly preferably in a range from 170 nm to 500 nm, and very particularly preferably in a range 200 nm to 400 nm.

In another embodiment, the average thickness for synthetic mica as the nonmetallic platelet-shaped substrate to be coated is situated preferably in a range from 100 nm to 700 nm, more preferably in a range from 120 nm to 600 nm, particularly preferably in a range from 140 nm to 500 nm, and very particularly preferably in a range from 150 nm to 450 nm.

Where nonmetallic platelet-shaped synthetic substrates below an average thickness of 50 nm are coated with, for example, high-index metal oxides, the resulting pigments are extremely fragile, and may break apart even on incorporation into the application medium, entailing in turn a significant reduction in luster. Moreover, the coating times for these thin substrates with, for example, high-index metal oxides are very long, owing to the high specific surface areas (surface area per unit weight of pigment) of these nonmetallic platelet-shaped synthetic substrates, and this causes high production costs. Above an average substrate thickness of 5000 nm, the pigments may become too thick overall. This may be associated with a poorer specific opacity, i.e. area covered per unit weight of pigment according to the invention, and also with a lower level of plane-parallel orientation in the application medium. The result of a poorer orientation, in turn, is a reduced luster.

The average thickness of the nonmetallic platelet-shaped synthetic substrate is determined on the basis of a cured varnish film in which the pigments are oriented substantially plane-parallel to the substrate. For this purpose, a polished section of the cured varnish film is examined under a scanning electron microscope (SEM), and the thickness of the nonmetallic platelet-shaped synthetic substrate is determined for 100 pigments and averaged.

It is preferred, furthermore, for the nonmetallic platelet-shaped synthetic substrate to have a high lightness, expressed as $L^*$ value, of at least 90, more preferably of at least 92, still more preferably of at least 95. The lightness here is determined by diffuse colorimetry on the basis of powder beds.

The surface of the nonmetallic platelet-shaped synthetic substrate, furthermore, is preferably very smooth and free from air inclusions, abrupt discontinuities, cracks and/or other constituents that give rise to light scattering.

In particular, synthetic mica platelets which comprise, within the stated limits, the composition set out in Table 1 have proven to be a highly suitable nonmetallic substrate for producing the silver-colored pigments according to the invention with metallic appearance.

The silver-colored pigments according to the invention may have any desired average particle size $D_{50}$. The $D_{50}$ values of the pigments according to the invention are situated preferably in a range from 3 to 80 μm. The pigments according to the invention preferably have a $D_{50}$ value from a range from 5 to 63 μm, with particular preference from a range from 7 to 56 μm, and very particularly preferably from a range from 9 to 49 μm.

The $D_{10}$ values of the pigments according to the invention are situated preferably in a range from 1 to 25 μm. The pigments according to the invention preferably have a $D_{10}$ value from a range from 2 to 21 μm, particularly preferably from a range from 3 to 18 μm, and very particularly preferably from a range from 4 to 14 μm.

The $D_{90}$ values of the pigments according to the invention are situated preferably in a range from 6 to 250 μm. The pigments according to the invention preferably have a $Dg_o$ value from a range from 15 to 210 μm.

The $D_{10}$, $D_{50}$, and $D_{90}$ values of the cumulative frequency distribution of the volume-averaged size distribution function as obtained by laser diffraction methods indicate that 10%, 50%, and 90%, respectively, of the pigments according to the invention have a diameter which is the same as or less than the respective figure indicated. In this case the size distribution curve of the pigments is determined using an instrument from Malvern (instrument: MALVERN Mastersizer 2000) in accordance with manufacturer instructions. The scattered-light signals were evaluated by the Fraunhofer method.

The silver-colored pigments according to the invention may optionally be provided with at least one external protective layer, further enhancing the light stability, weather stability and/or chemical stability of the pigment. The external protective layer may also be an aftercoating which facilitates the handling of the pigments according to the invention during incorporation into different media.

The external protective layer of the silver-colored pigments according to the invention can comprise, or preferably consist of, one or two metal oxide layers and/or metal hydroxide layers and/or metal oxide hydrate layers of the elements Si, Al, Zr or Ce. In one variant, a silicon oxide layer, preferably $SiO_2$ layer, is applied as the outermost metal oxide layer. A sequence is particularly preferred here, in which first a cerium oxide layer is applied, which is then followed by an $SiO_2$ layer, as described in EP 1 682 622 B1, the contents of which are hereby incorporated by reference.

The external protective layer may also be organic-chemically modified on the surface. For example, one or more silanes may be applied to this external protective layer. The silanes may be alkyl silanes having branched or unbranched alkyl radicals of 1 to 24 C atoms, preferably 6 to 18 C atoms.

The silanes may, however, also be organofunctional silanes, which make possible a chemical bonding to a plastic, a binder of a varnish or a paint, etc. These organofunctional groups can also be called coupling groups or functional binding groups and are preferably selected from the group consisting of hydroxyl, amino, acryl, methacryl, vinyl, epoxy, isocyanate, cyano and mixtures thereof.

The organofunctional silanes, preferably used as surface-modifying agents, which contain suitable functional groups are available commercially and are produced for example by Evonik and sold under the trade name "Dynasylan". Other products can be obtained from Momentive (Silquest silanes) or from Wacker, for example standard silanes and α-silanes from the GENIOSIL product group. Examples of these are 3-methacryloxypropyltrimethoxysilane (Dynasylan MEMO, Silquest A-174NT), vinyltri(m)ethoxysilane (Dynasylan VTMO and VTEO respectively, Silquest A-151 and A-171 respectively), methyltri(m)ethoxysilane (Dynasylan MTMS and MTES respectively), 3-mercaptopropyltrimethoxysilane (Dynasylan MTMO; Silquest A-189), 3-glycidoxypropyltrimethoxysilane (Dynasylan GLYMO, Silquest A-187), tris[3-(trimethoxysilyl)propyl]isocyanurate (Silquest Y-11597), bis[3-(triethoxysilyl)propyl)]tetrasulfide (Silquest A-1289), bis[3-(triethoxysilyl)propyldisulfide (Silquest A-1589), beta-(3,4-epoxycyclohexyl)ethyltrimethoxysilane (Silquest A-186), bis(triethoxysilyl)ethane (Silquest Y-9805), gamma-isocyanatopropyltrimethoxysilane (Silquest A-Link 35, GENIOSIL GF40), methacryloxymethyltri(m)ethoxysilane (GENIOSIL XL 33, XL 36), (methacryloxymethyl)(m)ethyldimethoxysilane (GENIOSIL XL 32, XL 34), (isocyanatomethyl)methyldimethoxysilane, (isocyanatomethyl)trimethoxysilane, 3-(triethoxysilyl)propyl succinic anhydride (GEN10SIL GF 20), (methacryloxymethyl)methyldiethoxysilane, 2-acryloxyethylmethyldimethoxysilane, 2-methacryloxyethyltrimethoxysilane, 3-acryloxypropylmethyldimethoxysilane, 2-acryloxyethyltrimethoxysilane, 2-methacryloxyethyltriethoxysilane, 3-acryloxypropyltrimethoxysilane, 3-acryloxypropyltripropoxysilane, 3-methacryloxypropyltriethoxysilane, 3-methacryloxypropyltriacetoxysilane, 3-methacryloxypropylmethyldimethoxysilane, vinyltrichlorosilane, vinyltrimethoxysilane (GENIOSIL XL 10), vinyltris(2-methoxyethoxy)silane (GENIOSIL GF 58), vinyltriacetoxysilane or mixtures thereof.

The following are preferably used as organofunctional silanes: 3-methacryloxypropyltrimethoxysilane (Dynasylan MEMO, Silquest A-174NT), vinyltri(m)ethoxysilane (Dynasylan VTMO and VTEO respectively, Silquest A-151 and A-171 respectively), methyltri(m)ethoxysilane (Dynasylan MTMS and MTES respectively), beta-(3,4-epoxycyclohexyl)ethyltrimethoxysilane (Silquest A-186), bis(triethoxysilyl)ethane (Silquest Y-9805), gamma-isocyanatopropyltrimethoxysilane (Silquest A-Link 35, GENIOSIL GF40), methacryloxymethyltri(m)ethoxysilane (GENIOSIL XL 33, XL 36), (methacryloxymethyl)(m)ethyldimethoxysilane (GENIOSIL XL 32, XL 34), 3-(triethoxysilyl)propyl succinic anhydride (GENIOSIL GF 20), vinyltrimethoxysilane (GENIOSIL XL 10) and/or vinyltris(2-methoxyethoxy)silane (GENIOSIL GF 58).

However, it is also possible to apply other organofunctional silanes to the silver-colored pigments according to the invention.

Furthermore, aqueous prehydrolyzates, for example available commercially from Degussa, can be used. These include, inter alia, aqueous aminosiloxane (Dynasylan Hydrosil 1151), aqueous amino/alkylfunctional siloxane (Dynasylan Hydrosil 2627 or 2909), aqueous diaminofunctional siloxane (Dynasylan Hydrosil 2776), aqueous, aqueous epoxyfunctional siloxane (Dynasylan Hydrosil 2926), amino/alkylfunctional oligosiloxane (Dynasylan 1146), vinyl/alkylfunctional oligosiloxane (Dynasylan 6598), oligomeric vinylsilane (Dynasylan 6490) or oligomeric short-chain alkylfunctional silane (Dynasylan 9896).

In one preferred embodiment, the organofunctional silane mixture contains, in addition to at least one silane without a functional binding group, at least one aminofunctional silane. The amino function is a functional group which can enter into one or more chemical interactions with most of the groups present in binders. This can involve a covalent bond, such as e.g. with isocyanate- or carboxylate-functions of the binder, or hydrogen bridge bonds such as with OH- or COOR-functions or also ionic interactions. An amino function is therefore very well-suited to the purpose of chemically binding the pigment to various binders.

The following compounds are preferably used for this: 3-aminopropyltrimethoxysilane (Dynasylan AMMO; Silquest A-1110), 3-aminopropyltriethoxysilane (Dynasylan AMEO), [3-(2-aminoethyl)-aminopropyl]trimethoxysilane (Dynasylan DAMO, Silquest A-1120), [3-(2-aminoethyl)-aminopropyl]triethoxysilane, triaminofunctional trimethoxysilane (Silquest A-1130), bis-(gamma-trimethoxysilylpropyl)amine (Silquest A-1170), N-ethyl-gamma-aminoisobutyltrimethoxysilane (Silquest A-Link 15), N-phenyl-gamma-aminopropyltrimethoxysilane (Silquest Y-9669), 4-amino-3,3-dimethylbutyltrimethoxysilane (Silquest A-1637), N-cyclohexylaminomethylmethyldiethoxysilane (GENIOSIL XL 924), N-cyclohexylaminomethyltriethoxysilane (GENIOSIL XL 926), N-phenylaminomethyltrimethoxysilane (GENIOSIL XL 973) or mixtures thereof.

In a further preferred embodiment, the silane without a functional binding group is an alkyl silane. The alkyl silane preferably has the formula $R_{(4-z)}Si(X)_z$. In this formula, z is an integer from 1 to 3, R is a substituted or unsubstituted, unbranched or branched alkyl chain of 10 to 22 C atoms, and X is a halogen and/or alkoxy group. Preferred alkyl silanes are those with alkyl chains of at least 12 C atoms. R may also be joined cyclically to Si, in which case z is usually 2.

For the incorporation of pigments aftercoated with silanes and/or provided with an external protective layer into cosmetic formulations, it is necessary to ensure that the silane in question and/or the material of the external protective layer is permissible under cosmetics regulations.

In addition to the mentioned silanes and silane mixtures, further organic-chemical modifying agents, such as for example substituted or unsubstituted alkyl radicals, polyethers, thioethers, siloxanes, etc. and mixtures thereof, can also be arranged at or on the surface of the silver-colored pigments according to the invention. However, inorganic-chemical modifying agents (e.g. $Al_2O_3$ or $ZrO_2$ or mixtures thereof), which can increase e.g. the dispersibility and/or compatibility in the respective application medium, can also be applied to the pigment surface.

Via the surface modification it is possible to establish and/or modify, for example the hydrophilic properties or hydrophobicity of the pigment surface. For example, via the surface modification it is possible to establish and/or modify the leafing or nonleafing properties of the silver-colored pigments according to the invention. By leafing is meant that the pigments according to the invention are arranged in an application medium, for example a varnish or a printer ink, at or near the interface or surface of the application medium.

The surface-modifying agents can also contain reactive chemical groups, such as for example acrylate, methacrylate, vinyl, isocyanate, cyano, epoxy, hydroxyl, amino groups or mixtures thereof. These chemically reactive groups make possible a chemical binding, in particular the formation of covalent bonds, to the application medium or components of the application medium, such as for example binders. For example, the chemical and/or physical properties of cured varnishes, paints or printer inks, such as resistance to environmental influences such as moisture, solar radiation, UV resistance, etc., or resistance to mechanical influences, for example scratches, etc., can hereby be improved.

The chemical reaction between the chemically-reactive groups and the application medium or components of the application medium can be induced for example by irradiation with energy, for example in the form of UV radiation and/or heat.

In a further embodiment, the present invention comprises silver-colored pigments based on nonmetallic platelet-shaped synthetic substrates coated with a titanium dioxide layer and with an ilmenite-containing layer, in which the amount of iron compounds, calculated as elemental iron, in the pigment, based on the total weight of the pigments, is less than 5% by weight, and which as a function of the coating have an iron/titanium weight ratio in accordance with $$\frac{\text{Iron content (\% by weight)}}{\text{Titanium content (\% by weight)}} \quad (I)$$

Fraction of the coating (% by weight)

from a range from 1 to 8.

In a further embodiment, the invention comprises silver-colored pigments based on synthetic mica platelets which, after coating with a water-soluble tin compound, a water-soluble titanium compound, and in situ a water-soluble iron compound, are obtained after calcining under reducing conditions, the pigments being characterized by their color-neutral silver hue and low chroma values, with a measurement geometry of 110° relative to the angle of emergence of the light irradiated at 45°, of $C^*_{110} \leq 2.4$, measured on the basis of coatings applied to metal panels.

In a further embodiment, the invention comprises silver-colored pigments based on synthetic mica platelets having a lightness $L^*$ of more than 90, preferably more than 92, more preferably more than 95, which, after application and drying, give a coating system an unusual strong glitter effect.

In another embodiment, the invention comprises silver-colored pigments which in terms of their visual appearance are indistinguishable or not substantially distinguishable from metallic effect pigments, and whose flop index, as a function of the average particle size $D_{50}$, is virtually identical to that of aluminum effect pigments.

In one preferred embodiment, the ilmenite-containing layer of the silver-colored pigments according to the invention is located on the outside in the layer construction and is optionally surrounded with at least one protective layer. In a particularly preferred embodiment, the silver-colored pigments according to the invention comprise a single layer of titanium dioxide in the rutile modification, a single ilmenite-containing layer, optionally at least one protective layer, with at least partial penetration between the titanium dioxide layer and the ilmenite-containing layer, and with a concentration gradient between the two layers.

The silver-colored pigments according to the invention can also be used advantageously in blends with transparent and opaque white, chromatic and black pigments, and also with further effect pigments.

The silver-colored pigments according to the invention can be used to produce pigment preparations and dry preparations.

Furthermore, the silver-colored pigments according to the invention can be used for example in cosmetic formulations, plastics, ceramic materials, glasses and coating compositions such as paints, printer inks, e.g. for offset, screen, gravure, flexo and security printing, for bronzing, in inks, in toners, varnishes, e.g. automotive coatings or powder coatings, for laser marking of paper and plastics, for seed dyeing, for dyeing food or pharmaceutical products or for coloring (agricultural) films, tarpaulins or textiles.

In cosmetic formulations, the silver-colored pigments according to the invention can be combined with raw materials, auxiliaries and active ingredients that are suitable for the particular application. The concentration of the silver-colored pigments according to the invention in the formulation may be between 0.001% by weight for rinse-off products and 40.0% by weight for leave-on products, based in each case on the total weight of the formulation.

The silver-colored pigments according to the invention are suitable in particular for use in cosmetics, such as, for example, body powder, face powder, compact and loose powder, face makeup, powder cream, cream makeup, emulsion makeup, wax makeup, foundation, mousse makeup, rouge, eye makeup such as eye shadow, mascara, eyeliner, liquid eyeliner, eyebrow pencil, lip care stick, lipstick, lip gloss, lip liner, hair styling compositions such as hairspray, hair mousse, hair gel, hair wax, hair mascara, permanent or semi-permanent hair colors, temporary hair colors, skincare compositions such as lotions, gels, and emulsions, and also nail varnish compositions.

In order to obtain specific color effects it is possible in the cosmetic applications, in addition to the silver-colored pigments according to the invention, to use other colorants and/or conventional effect pigments and/or mixtures thereof in variable proportions. Conventional effect pigments that can be used include, for example, commercial pearlescent pigments based on natural mica platelets coated with high-index metal oxides (e.g., the Prestige product group from Sudarshan Chemical Industries Limited, India), BiOCl platelets, $TiO_2$ platelets, pearlescent pigments based on synthetic mica platelets coated with high-index metal oxides (e.g., the SynCrystal product group from Eckert) or based on glass platelets coated with high-index metal oxides (e.g., the MIRAGE product group from Eckart), based on $Al_2O_3$ or $SiO_2$ platelets coated with high-index metal oxides, or based on BiOCl or $TiO_2$ platelets coated with high-index and/or low-index metal oxides. A further possibility is to add metallic effect pigments, such as the Visionaire product group from Eckert, for example. The colorants may be selected from inorganic or organic pigments.

EXAMPLES

The examples which follow are intended to elucidate the invention in more detail, though without restricting it. All percentages are to be understood as % by weight.

I Preparation of the Nonmetallic Platelet-Shaped Synthetic Substrates and the Pigments

Example 1

Preparation and Classification of Synthetic Fluorophlogopite Mica $KMg_3(AlSi_3O_{10})F_2$ 40 parts of anhydrous silica, 30 parts of magnesium oxide, 13 parts of aluminum oxide and 17 parts of potassium hexafluorosilicate were mixed and melted at 1500° C. After cooling to 1350° C., crystallization of fluorophlogopite ($KMg_3(AlSi_3O_{10})F_2$) commenced. The fluorophlogopite was then comminuted and delaminated using a laboratory edge runner mill from American Cyanamid Company.

The resulting platelet-shaped fluorophlogopite was calcined in a muffle furnace at 1100° C. for an hour and then classified using a laboratory sieve.

In the course of the classification, two fractions were obtained, with the following particle size distribution (MALVERN Mastersizer MS 2000):

Fraction 1: $D_{10}=11.4$ µm, $D_{50}=21.8$ µm, $D_{90}=40.0$ µm,
Fraction 2: $D_{10}=5.6$ µm, $D_{50}=12.2$ µm, $D_{90}=24.8$ µm The composition of the synthetic mica platelets, measured by XRF, can be found in Table 3.

Example 2

Preparation of Synthetic Fluorophlogopite Mica $KMg_20.5(AlSi_2O_{10})F_2$ 30 parts of anhydrous silica, 25 parts of magnesium oxide, 10 parts of aluminum oxide and 15 parts of potassium hexafluorosilicate were mixed with one another and melted at 1500° C. The liquid mixture was subsequently crystallized slowly at temperatures of 1350° C. to produce synthetic fluorophlogopite ($KMg_20.5(AlSi_2O_{10})F_2$). The synthetic mica lumps obtained were comminuted and subsequently delaminated using a laboratory edge runner mill from American Cyanamid Company.

The resulting platelet-shaped fluorophlogopite was subsequently calcined in a muffle furnace at 1100° C. for an hour and then classified accordingly using a laboratory sieve. In the course of the classification, two fractions were obtained, with the following particle size distribution (MALVERN Mastersizer MS 2000):

Fraction 1: $D_{10}=10.2$ µm, $D_{50}=20.7$ µm, $D_{90}=42.2$ µm,
Fraction 2: $D_{10}=6.5$ µm, $D_{50}=13.4$ µm, $D_{90}=25.8$ µm The composition of the synthetic mica platelets, measured by XRF, can be found in Table 3.

Example 3

Classification of Glass Platelets

A suspension of 200 g of glass platelets (average thickness: 1 µm, standard deviation in thickness: about 40%) in DI water (about 3% by weight, DI: fully demineralized) was classified using a 100-µm sieve, and the material passing through the sieve was sieved in turn through a 63-µm sieve. The material passing through this sieve in turn was sieved through a 36-µm sieve. This sieving procedure was repeated twice with sieve residue obtained on the 36-µm sieve. In this way a glass platelet fraction was obtained that had the following particle size distribution (MALVERN Mastersizer MS 2000): $D_{10}=17$ µm, $D_{50}=33$ µm, $D_{90}=59$ µm.

Example 4

Coating of the Synthetic Mica from Example 9 with Ilmenite 270 g of the synthetic mica from Example 1 (fraction 1) was suspended in 1350 ml of DI water and heated to 80° C. with turbulent stirring. The pH was lowered to 1.9 using dilute hydrochloric acid. Then an "$SnO_2$" layer was deposited on the substrate surface. This layer was formed by adding a solution of 3 g of $SnCl_4 \times 5H_2O$ (in 10 ml of conc. HCl plus 50 ml of DI water) with simultaneous metering of a 10% strength aqueous sodium hydroxide solution. Thereafter the pH was lowered to pH 1.6 using dilute hydrochloric acid, after which a solution of 400 ml of $TiCl_4$ (200 g of $TiO_2$/l of DI water) and also, at the same time, a 10% strength aqueous sodium hydroxide solution were metered into the suspension. After the end of the coating procedure, stirring was continued for 1 hour, after which the pH was adjusted to 2.9 using dilute sodium hydroxide solution. Thereafter 30 ml of $FeCl_3$ (280 g of $Fe_2O_3$/l of DI water) and also, simultaneously, a 10% strength aqueous sodium hydroxide solution were metered into the suspension, which was stirred for 1 hour and filtered, and the filter cake was washed with DI water. The filter cake was calcined in a tube furnace at 800° C. under an atmosphere of forming gas (70% of $N_2$ 130% of $H_2$) for 2 hours. This gave silver-colored pigments of extremely high luster with a metallic appearance. The pigments had the following particle size distribution (MALVERN Mastersizer MS 2000): $D_{10}=12.4$ µm, $D_{50}=23.9$ µm, $D_{90}=43.1$ µm.

Example 5

Coating of the Synthetic Mica from Example 2 with Ilmenite 270 g of the synthetic mica from Example 2 (fraction 2) was suspended in 2000 ml of DI water and heated to 80° C. with turbulent stirring. The pH was lowered to 1.9 using dilute hydrochloric acid. Then an "$SnO_2$" layer was deposited on the substrate surface. This layer was formed by adding a solution of 5 g of $SnCl_4 \times 5H_2O$ (in 10 ml of conc. HCl plus 50 ml of DI water) with simultaneous metering of a 10% strength aqueous sodium hydroxide solution. Thereafter a solution of 650 ml of $TiCl_4$ (200 g of $TiO_2$/l of DI water) and also, at the same time, a 10% strength aqueous sodium hydroxide solution were metered into the suspension. After the end of the coating procedure, stirring was continued for 1 hour, after which the pH was adjusted to 2.9 using dilute sodium hydroxide solution. Thereafter 30 ml of $FeCl_3$ (280 g of $Fe_2O_3$/l of DI water) and also, at the same time, a 10% strength aqueous sodium hydroxide solution were metered into the suspension, which was stirred for 1 hour and filtered, and the filter cake was washed with DI water. The filter cake was calcined in a tube furnace at 800° C. under an atmosphere of forming gas (70% of $N_2$/30% of $H_2$) for 2 hours.

This gave lustrous silver-colored pigments with a metallic appearance and a high opacity. The pigments had the following particle size distribution (MALVERN Mastersizer MS 2000): $D_{10}=7.3$ µm, $D_{50}=13.3$ µm, $D_{90}=25.4$ µm.

Example 6

Coating of the Glass Platelets from Example 3 with Ilmenite 200 g of glass platelets from Example 3 were suspended in 1800 ml of DI water and heated to 70° C. with turbulent stirring. The pH was lowered to 1.9 with dilute hydrochloric acid. Then an "$SnO_2$" layer was deposited on the substrate surface. This layer was formed by adding a solution of 5 g of $SnCl_4 \times 5H_2O$ (in 15 ml of conc. HCl plus 65 ml of DI water) with simultaneous metered addition of a 10% strength aqueous sodium hydroxide solution. This was followed by stirring for 10 minutes, after which a solution of 100 ml of $TiCl_4$ (200 g of $TiO_2$/l of DI water) was metered into the suspension in parallel with 10% strength aqueous sodium hydroxide solution. After the end of the coating procedure, stirring was continued for 1 hour, after which the pH was adjusted to 2.9 with dilute sodium hydroxide solution. Thereafter 10 ml of $FeCl_3$ (280 g of $Fe_2O_3$/l of DI water) were metered into the suspension in parallel with 10% strength aqueous sodium hydroxide solution, followed by stirring for 1 hour and filtration, and the filter cake was washed with DI water. The filter cake was calcined in a tube furnace at 550° C. under an atmosphere of forming gas (70% of $N_2$/30% of $H_2$) for 2 hours.

This gave strongly glittery, silver-colored pigments with a metallic appearance and an extremely high luster. The pigments had the following particle size distribution (MALVERN Mastersizer MS 2000): $D_{10}=18.4$ µm, $D_{50}=34.3$ µm, $D_{90}=61.4$ µm.

Comparative Example 1

Coating of Natural Muscovite Mica with a MALVERN Mastersizer MS 2000 Particle Size Distribution of $D_{10}=11.0$ µm, $D_{50}=23.1$ µm, $D_{90}=44.4$ µm with Ilmenite Coating took place in exactly the way described in Example 7 from WO 2004/099319 A2. This gave silver-colored, opaque pearlescent pigments with a low luster and a low flop index. The pigments had the following particle size distribution (MALVERN Mastersizer MS 2000): $D_{10}=11.6$ µm, $D_{50}=24.2$ µm, $D_{90}=46.7$ µm.

Comparative Example 2

Aluminum effect pigment Stapa Metallux 2154 from Eckert. The pigments have the following particle size distribution (Cilas 1064): $D_{10}=12.4$ µm, $D_{50}=19.8$ µm, $D_{90}=30.0$ µm.

Comparative Example 3

Ilmenite-coated pearlescent pigment Iriodin 9602 WR from Merck. The pigments have the following particle size distribution (MALVERN Mastersizer MS 2000): $D_{10}=10.1$ µm, $D_{50}=21.3$ µm, $D_{90}=40.8$ µm.

Comparative Example 4

Iimenite-coated pearlescent pigment Iriodin 9612 WR from Merck. The pigments have the following particle size distribution (MALVERN Mastersizer MS 2000): $D_{10}=3.0$ µm, $D_{50}=6.4$ µm, $D_{90}=12.4$ µm.

Comparative Example 5

Silver pearlescent pigment Phoenix CFE 1001 from Eckart. The pigments have the following particle size distribution (MALVERN Mastersizer MS 2000): $D_{10}=9.6$ µm, $D_{50}=20.3$ µm, $D_{90}=38.3$ µm.

Comparative Example 6

Coating of Natural Muscovite Mica with a MALVERN Mastersizer MS 2000 Particle Size Distribution of $D_{10}=11.0$ µm, $D_{50}=23.1$ µm, $D_{90}=44.4$ µm with Ilmenite Coating took place in exactly the way described in Example 1 from WO 2004/099319 A2. This gave silver-colored, violet-tinged pearlescent pigments with a low luster and a low flop index. The pigments have the following particle size distribution (MALVERN Mastersizer MS 2000): $D_{10}=11.4$ µm, $D_{50}=23.8$ µm, $D_{90}=45.7$ µm.

Comparative Example 7

Identical to multilayer pearlescent pigment from Example 10 of DE 10 2009 037 935 A1; average particle size (MALVERN Mastersizer MS 2000): $D_{50}=29.2$ µm.

Comparative Example 8

Identical to pearlescent pigment from Example 1a of DE 10 2009 049 413 A1; average particle size (MALVERN Mastersizer MS 2000): $D_{50}=3.2$ µm.

II Characterization of the Nonmetallic Platelet-Shaped Synthetic Substrates and of the Pigments from the Examples and Comparative Examples IIa Particle Size Measurement The size distribution curve of the nonmetallic platelet-shaped synthetic substrates and of the pigments was determined using an instrument from Malvern (instrument: MALVERN Mastersizer 2000) in accordance with manufacturer instructions. For this purpose, about 0.1 g of the substrate or pigment in question, in the form of an aqueous suspension without dispersing agents added, was introduced using a Pasteur pipette, and with continuous stirring, into the sample preparation cell of the instrument, and subjected to measurement a number of times. The resultant averages were formed from the individual measurement results. The scattered-light signals were evaluated here in accordance with the Fraunhofer method.

The size distribution curve of the metallic effect pigment (in paste form) from Comparative example 2 was measured using an instrument from Quantachrome (instrument: Cilas 1064) in accordance with manufacturer instructions. For this purpose about 1.5 g of the pigment was suspended in isopropanol, treated in an ultrasound bath (instrument: Sonorex IK 52 from Bandelin) for 300 seconds, and then introduced using a Pasteur pipette into the sample preparation cell of the instrument and subjected to measurement a number of times. The resultant averages were formed from the individual measurement results. The scattered-light signals were evaluated here in accordance with the Fraunhofer method.

The average size $D_{50}$ in the context of this invention refers to the $D_{50}$ value of the cumulative frequency distribution of the volume-averaged size distribution function as obtained by laser diffraction methods. The $D_{50}$ value indicates that 50% of the nonmetallic platelet-shaped synthetic substrates or pigments have a diameter which is the same as or less than the specified value, 20 µm for example. Correspondingly, the $D_{90}$ value indicates that 90% of the substrates or pigments have a diameter which is the same as or less than the respective value. Furthermore, the $D_{10}$ value indicates that 10% of the substrates or pigments have a diameter which is the same as or less than the respective value.

IIb Determination of the Average Thickness of the Nonmetallic Platelet-Shaped Synthetic Substrates For the determination of the average thickness of the nonmetallic platelet-shaped synthetic substrates, the substrates or pigments were incorporated at 10% by weight into an Autoclear Plus HS two-component clear-coat varnish from Sikkens, using a sleeved brush, and, using a spiral doctor blade, were applied to a film (26 µm wet-film thickness) and dried. After drying for 24 hours, polished sections were prepared from these doctor-blade drawdowns and were subjected to measurement by scanning electron microscopy. In this procedure, at least 100 pigment particles were measured in order to obtain meaningful statistics. The average thickness of the synthetic mica platelets used as substrate can be seen from Table 2.

TABLE 2

|         | Example 1 Fraction 1 Average thickness [nm] | Example 1 Fraction 2 Average thickness [nm] | Example 2 Fraction 1 Average thickness [nm] | Example 2 Fraction 2 Average thickness [nm] |
|---------|---------|---------|---------|---------|
| $D_{10}$ | 289 | 154 | 321 | 138 |
| $D_{50}$ | 434 | 219 | 443 | 209 |
| $D_{90}$ | 734 | 318 | 779 | 294 |

The indication $D_{10}$ here means that 10% of the nonmetallic platelet-shaped synthetic substrates have an average thickness which is equal to or smaller than the stated value.

Correspondingly, the $D_{50}$ or $D_{90}$ value here indicates that 50% or 90%, respectively, of the nonmetallic platelet-shaped synthetic substrates have an average thickness which is the same as or smaller than the specified value.

IIc Determination of the Metal Oxide Content

The metal oxide contents of the nonmetallic platelet-shaped synthetic substrates or pigments were determined by means of X-ray fluorescence (XRF) analysis.

For this purpose the substrate or pigment was incorporated into a lithium tetraborate glass tablet, fixed in solid sample measuring beakers and measured therefrom. The instrument used as measuring instrument was the Advantix ARL from Thermo Scientific.

TABLE 3

Metal oxide contents by XRF of the synthetic mica platelets used as substrate

| Metal oxide | Example 1 (% by weight) | Example 2 (% by weight) |
|---|---|---|
| $TiO_2$ | <0.1 | <0.1 |
| $SnO_2$ | <0.1 | <0.1 |
| $SiO_2$ | 42.1 | 20.3 |
| $Al_2O_3$ | 12.2 | 8.1 |
| $K_2O$ | 11.0 | 15.9 |
| $Fe_2O_3$ | 0.1 | 0.1 |
| $Cr_2O_3$ | <0.1 | <0.1 |
| $CeO_2$ | <0.1 | <0.1 |
| CaO | 0.1 | <0.1 |
| MgO | 31.6 | 27.6 |
| $Na_2O$ | 0.2 | 0.4 |
| $P_2O_5$ | <0.1 | <0.1 |
| MnO | <0.1 | <0.1 |

The % by weight figures reported in Table 3 relate in each case to the total weight of the nonmetallic platelet-shaped substrate.

TABLE 4

Magnesium oxide content of the pigments by XRF

|  | MgO (% by weight) |
|---|---|
| Example 4 | 19.6 |
| Example 5 | 17.1 |
| Comparative example 1 | 0.3 |
| Comparative example 3 | 0.3 |
| Comparative example 4 | 0.2 |
| Comparative example 5 | 0.3 |

The % by weight figures reported in Table 4 relate in each case to the total weight of the respective pigment.

TABLE 5

Iron/titanium weight ratio of the pigments

|  | Example 4 | Example 5 | Example 6 | Comparative example 1 | Comparative example 3 | Comparative example 4 | Comparative example 6 |
|---|---|---|---|---|---|---|---|
| $Fe_2O_3$ (% by weight) | 2.9 | 3.2 | 2.8 | 4.3 | 5.9 | 9.9 | 3.7 |
| $FeTiO_3$ (% by weight) | 5.4 | 6.1 | 5.3 | 8.1 | 11.3 | 18.8 | 7.1 |
| Fe (% by weight), calculated | 2.0 | 2.2 | 2.0 | 3.0 | 4.1 | 6.9 | 2.6 |
| $TiO_2$ (% by weight) | 23.9 | 33.4 | 9.7 | 30.2 | 24.7 | 30.4 | 28.0 |
| Fe/Ti weight ratio | 0.14 | 0.11 | 0.34 | 0.17 | 0.28 | 0.38 | 0.16 |
| Fe/Ti weight ratio (layer) | 4.37 | 4.21 | 4.60 | 6.16 | 9.54 | 16.28 | 5.01 |

The weight fractions reported in Table 5 relate in each case to the total weight of the pigment.

The iron values reported in Table 5 are values converted arithmetically to elemental iron. For this purpose, the contents data for all the iron compounds detectable in the pigment by XRF were converted arithmetically to elemental iron. For the calculation of the Fe/Ti weight ratio reported in Table 5, the titanium oxide content of the pigment as measured by means of XRF was converted arithmetically to elemental titanium.

For the Fe/Ti weight ratio (layer) reported in Table 5, account was taken of the fraction of the coating on the pigments, in accordance with $$\frac{\text{Iron content (\% by weight)}}{\text{Titanium content (\% by weight)}} \text{Fraction of the coating (\% by weight)}$$

The fraction of the coating (% by weight) is defined by the total weight of the pigment (100% by weight) minus the fraction of the substrate (% by weight).

IId Determination of the Lead Contents Via Solids AAS

The lead contents of the synthetic mica platelets and of the pigments based on synthetic mica platelets were determined using solids graphite tube atomic absorption spectrometry. The instrument used was a ZEENIT 650 with SSA 600 solids sampler (manufacturer: Analytik Jena). The corresponding contents figures for the synthetic mica platelets or the pigments according to the invention based thereon can be seen from Table 6.

TABLE 6

|  | Lead content [ppm] |
| --- | --- |
| Example 1 | <1 |
| Example 2 | <1 |
| Example 4 | <1 |
| Example 5 | <1 |

IIe Determination of the Chemicals Resistance

The chemicals resistance of the pigments from the examples and comparative examples was determined on the basis of coatings applied to metal panels. 6 g of the pigment in question (in powder form) was incorporated by stirring into a mixture of 90 g of a conventional wet varnish based on hydroxyfunctional acrylates (CSR varnish, colorless) and 10 g of butyl acetate 85. The viscosity was then adjusted to 17" using a mixture of butyl acetate 85 and xylene in a ratio of 1:1 in the DIN 4-mm cup.

100 g of this coating material in each case was applied to cover the metal panels in the same way as for IIIa using an automatic sprayer. After coating had taken place, the metal panels were baked at 80° C. for 30 minutes.

24 hours later, one drop each of 10% strength by weight HCl and one drop of a 1 M sodium hydroxide solution were applied, staggered, to each panel. After an exposure time of 0.5 h, 1 h, 2 h and 3 h, respectively, the HCl or NaOH drops were washed off with DI water and the panels were each inspected visually for damage to the coating film. Extreme damage, i.e. complete breakdown of the pigment, was given a score of 10, while no difference relative to the untreated panel was given a score of 0. The results of this visual inspection are reproduced in Table 7.

TABLE 7

| | Chemicals resistance | | |
| --- | --- | --- | --- |
| Pigment from | Acid | Alkali | Sum |
| Example 4 | 0 | 0 | 0 |
| Example 5 | 0 | 2 | 2 |
| Example 6 | 0 | 1 | 1 |
| Comparative example 1 | 0 | 4 | 4 |
| Comparative example 2 | 5 | 10 | 15 |
| Comparative example 3 | 0 | 6 | 6 |

TABLE 7-continued

| | Chemicals resistance | | |
| --- | --- | --- | --- |
| Pigment from | Acid | Alkali | Sum |
| Comparative example 4 | 3 | 4 | 7 |
| Comparative example 5 | 0 | 0 | 0 |
| Comparative example 6 | 0 | 3 | 3 |

The pigments according to the invention and also the conventional transparent silver-colored pearlescent pigment of the Phoenix series from Eckart (Comparative example 5) are notable for their extremely high chemicals resistance.

IIf Temperature Stability

For the purpose of testing the temperature stability, the pigments were stored at temperatures of 100° C. and 200° C. for 30 minutes in each case. On the basis of doctor-blade drawdowns of the respective pigment in a conventional nitrocellulose varnish (Dr Renger Erco bronzing mixed varnish 2615e; Morton, pigmentation level of 10% by weight, based on the total weight of the wet varnish) on black-white opacity charts (Byko-Chart 2853, Byk Gardner), any color changes that took place were assessed visually.

In this case it was found that on doctor-blade drawdowns of the silver-colored pigments according to the invention there was no observable change in color either after storage of the pigments at 100° C. or after storage of the pigments at 200° C.

IIg Lightness L*

The lightness L* of the nonmetallic platelet-shaped synthetic substrates was measured by diffuse colorimetry of the respective powder beds using the CR 310 colorimeter from Konica Minolta.

TABLE 8

|  | Lightness L*, diffuse |
| --- | --- |
| Example 1 | 97.6 |
| Example 2 | 98.4 |
| Example 3 | 96.7 |

IIh Diffuse Colorimetry

The lightness L*, a* and b* values and the chroma were determined by diffuse colorimetry of the respective powder beds, using a CM700d colorimeter from Konica Minolta.

TABLE 9

| Example/Comparative example | L* | a* | b* | C* | h° |
| --- | --- | --- | --- | --- | --- |
| Example 6 | 48.9 | −0.3 | 0.1 | 0.3 | 165.2 |
| Comparative example 7 | 49.5 | 12.4 | 14.3 | 19.0 | 49.2 |
| Comparative example 3 | 60.8 | −0.5 | 1.5 | 1.6 | 108.1 |
| Comparative example 4 | 50.6 | −1.6 | −4.1 | 4.4 | 249.4 |

Example 6 according to the invention is notable for low a* and b* values and hence also for low chroma values. The multilayer pearlescent pigment from Comparative example 7 does have a silver interference color, but it is also clearly apparent from the chroma value that the pigment has a reddish brown absorption color. In the case of Comparative examples 3 and 4 as well, in contrast to Example 6 according to the invention, at least one of the values, C*, a* or b*, is always increased, and so here as well it was possible to demonstrate the visually perceptible color tinge in a technical measurement.

IIi Corrosion Resistance

The corrosion resistance of the silver-colored pigments according to the invention was determined by determination of the gassing behavior in an aqueous carbomer gel system. For this purpose, first of all, a carbomer gel consisting of 0.7% by weight of Aristoflex AVC gel former from Clariant and 99.3% by weight of DI water was prepared with stirring. Then a suspension of 23% by weight of silver-colored pigment and 77% by weight of Di water was added with stirring to the carbomer gel. This mixture was admixed with 1% by weight, based on its total weight, of the preservative Uniphen P-23 in order to prevent microbial contamination and possibly falsification of the measurement result as a result of gas secretion by the microbes. Subsequently, 300 g of the resulting mixture was introduced into a gas wash bottle, closed off with a double-chamber gas bubble counter, and then heated to 40° C. in a water bath. The evolution of gas was determined over a period of 30 days. After these 30 days, there was no gas evolution observed with the silver-colored pigments.

The test is passed if the gas evolution after 30 days is <10 ml. Ideally no gas evolution is observed.

III Characterization of the Optical Effect of the Pigments from the Examples and Comparative Examples IIIa Determination of the Light/Dark Flop (Flop Index)

The flop index of the pigments from the examples and comparative examples was determined on the basis of coatings applied to metal panels. 6 g of the respective pigment (in powder form) was incorporated by stirring into a mixture of 90 g of a conventional wet varnish based on hydroxyfunctional acrylates (CSR varnish, colorless) and 10 g of butyl acetate 85. The viscosity was subsequently adjusted to 17" using 25 g of a mixture of butyl acetate 85 and xylene in a ratio of 1:1 in the DIN 4-mm cup. 100 g of this coating material in each case was applied to metal panels using an automatic sprayer and the LP-90 spray gun with 1.3.5 needle setting (both from Languth) with a pressure of 4 bar (6 passes). After a flash-off time of 15 minutes, a further clear coat layer (70 g of KL Autoclear Plus and 42 g of P25 hardener, each from Sikkens) was applied with a pressure of 4 bar in 3 passes (needle setting: 2.0.3). After coating had taken place, the metal panels were baked at 80° C. for 30 minutes.

The flop index is defined in accordance with Alman as follows (S. Schellenberger, M. Entenmann, A. Hennemann, P. Thometzek, Farbe and Lack, 04/2007, p. 130):

$$\text{Flop index}=2.69\cdot(L_{E1}-L_{E3})^{1.11}/L_{E2}^{0.86}$$

where $L_{E1}$ is the lightness of the near-specular measuring angle (E1=15° relative to the specular angle), $L_{E2}$ is the lightness of the measuring angle between near-specular and far-specular angle (E2=45° relative to the specular angle), and $L_{E3}$ is the lightness of the far-specular measuring angle (E3=110° relative to the specular angle).

The larger the numerical value of the flop index, the more greatly the light/dark flop is expressed.

For the determination of the flop index, the lightness L* was measured by multiangle colorimetry using the Byk-mac instrument from Byk Gardner. The corresponding values are listed in Table 10.

Examples 4 and 6 in fact have a higher flop index than a comparable metallic pigment (Comparative example 2). Example 5 possesses a lower flop index, this being attributable to the smaller particle size and the greater degree of scattering associated therewith. As compared with a metallic effect pigment having a similar particle size distribution, the flop index of the pigment according to the invention, here as well, is slightly above that of the comparable metallic effect pigment.

Comparative example 3 possesses a comparably high flop index. The latter is favored by the greater coloration of the pigment. In visual terms, however, the pigment is not color-neutral (chroma) and therefore almost wholly unsuitable as an imitation or substitute for an aluminum effect pigment.

IIIb Effect Measurements

Effect measurements for determining the glitter effect of the pigments were carried out on the basis of the spray applications from IIIa, using a BYK-mac (Byk-Gardner).

To simulate effect changes upon direct illumination, the glitter effect is investigated with the BYK-mac, using a high-resolution CCD camera. The glitter effect, caused by the reflecting ability of the individual effect pigments, is perceived only upon direct solar irradiation, and changes depending on the angle of illumination. For this reason, the sample in the Byk-mac is illuminated with very bright LEDs at three different angles (15°/45°/75°). Using the CCD camera, an image is recorded in each case perpendicularly to the surface. The images are analyzed using image processing algorithms, with the histogram of the lightness stages being used as a basis for calculating the glitter parameters. In order to ensure improved differentiation, the glitter effect was described using a two-dimensional system, the glitter area S_a and the glitter intensity S_i. Alternatively, the named data were summarized in a one-dimensional value, the glitter degree S_G. The corresponding measurement values are collated in Table 10.

Critical to the visual impression is the one-dimensional glitter degree S_G. The higher the numerical value of S_G, the higher the glitter effect perceptible to the eye. In a two-dimensional representation, the glitter degree S_G can be broken down into the components of glitter intensity S_i and glitter area S_a. Since both components have a critical influence on the glitter degree S_G, it may happen that an effect pigment has virtually the same glitter degree S_G in the 15°, 45' and 75° measurement geometries, despite the fact that the numerical values of S_a and S_G in the measurement geometries under consideration are significantly increased or lowered.

In terms of their glitter intensity S_i, the silver-colored pigments according to the invention are superior to pearlescent pigments based on natural mica platelets. In a comparison of glitter area S_a, glitter intensity S_i, glitter degree S_G, and flop index, it is necessary to take into account the average particle size $D_{50}$. In other words, only pigments with the same or similar average particle size are comparable with one another. A lower average particle size $D_{50}$, such as in Example 5, is manifested in lower figures for glitter area S_a, glitter intensity S_i, glitter degree S_G, and flop index.

The measurement values for lightness, chroma, flop index, S_G, S_a, and S_i that are shown in Table 10 were determined on the basis of the spray applications in IIIa.

TABLE 10

Lightness L*, chroma, flop index, glitter area S_a, glitter intensity S_i, glitter degree S_G of the pigments

|  | Measurement geometry | Lightness L* | Chroma | Flop index | S_G [15°] | S_i [15°] | S_a [15°] |
|---|---|---|---|---|---|---|---|
| Example 4 | 15° | 132.8 | 0.5 | 21.4 | 6.7 | 14.7 | 31.1 |
|  | 25° | 92.0 | 0.8 |  |  |  |  |
|  | 45° | 45.3 | 1.3 |  |  |  |  |
|  | 75° | 26.1 | 1.9 |  |  |  |  |
|  | 110° | 20.2 | 1.6 |  |  |  |  |

TABLE 10-continued

Lightness L*, chroma, flop index, glitter area S_a, glitter intensity S_i, glitter degree S_G of the pigments

| | Measurement geometry | Lightness L* | Chroma | Flop index | S_G [15°] | S_i [15°] | S_a [15°] |
|---|---|---|---|---|---|---|---|
| Example 5 | 15° | 120.3 | 0.67 | 15.8 | 4.4 | 9.1 | 24.1 |
| | 25° | 92.7 | 0.51 | | | | |
| | 45° | 53.4 | 0.91 | | | | |
| | 75° | 30.8 | 1.21 | | | | |
| | 110° | 22.9 | 0.93 | | | | |
| Example 6 | 15° | 116.0 | 0.4 | 20.0 | 12.3 | 33.0 | 21.2 |
| | 25° | 78.6 | 0.9 | | | | |
| | 45° | 37.5 | 1.7 | | | | |
| | 75° | 27.1 | 2.1 | | | | |
| | 110° | 24.4 | 1.6 | | | | |
| Comparative example 1 | 15° | 126.0 | 1.0 | 16.8 | 3.7 | 7.7 | 24.1 |
| | 25° | 95.8 | 0.5 | | | | |
| | 45° | 53.3 | 0.8 | | | | |
| | 75° | 30.7 | 1.0 | | | | |
| | 110° | 23.2 | 0.8 | | | | |
| Comparative example 2 | 15° | 149.8 | 0.4 | 19.1 | 5.2 | 11.0 | 26.6 |
| | 25° | 109.7 | 0.36 | | | | |
| | 45° | 56.9 | 0.50 | | | | |
| | 75° | 34.0 | 0.73 | | | | |
| | 110° | 28.5 | 1.22 | | | | |
| Comparative example 3 | 15° | 120.3 | 1.76 | 20.2 | 4.7 | 10.0 | 24.7 |
| | 25° | 87.0 | 2.10 | | | | |
| | 45° | 43.4 | 2.36 | | | | |
| | 75° | 23.3 | 2.68 | | | | |
| | 110° | 16.9 | 2.41 | | | | |
| Comparative example 4 | 15° | 83.8 | 1.41 | 10.3 | 0.8 | 2.7 | 7.9 |
| | 25° | 72.5 | 0.82 | | | | |
| | 45° | 50.4 | 1.69 | | | | |
| | 75° | 30.7 | 2.57 | | | | |
| | 110° | 20.3 | 2.15 | | | | |
| Comparative example 5 | 15° | 140.4 | 1.5 | 9.8 | 3.8 | 8.1 | 20.9 |
| | 25° | 109.6 | 1.3 | | | | |
| | 45° | 72.3 | 2.1 | | | | |
| | 75° | 59.5 | 3.1 | | | | |
| | 110° | 60.1 | 2.5 | | | | |
| Comparative example 6 | 15° | 125.8 | 0.5 | 16.2 | 3.1 | 6.6 | 18.3 |
| | 25° | 96.5 | 0.9 | | | | |
| | 45° | 54.2 | 1.8 | | | | |
| | 75° | 31.8 | 2.6 | | | | |
| | 110° | 24.9 | 2.1 | | | | |
| Comparative example 7 | 15° | 97.1 | 18.0 | 11.6 | 6.6 | 13.7 | 32.5 |
| | 25° | 69.8 | 28.5 | | | | |
| | 45° | 43.3 | 49.6 | | | | |
| | 75° | 36.7 | 59.5 | | | | |
| | 110° | 34.5 | 62.1 | | | | |
| Comparative example 8 | 15° | 119.8 | 1.2 | 1.9 | 0.9 | 2.1 | 7.8 |
| | 25° | 105.8 | 0.9 | | | | |
| | 45° | 84.7 | 1.2 | | | | |
| | 75° | 73.7 | 0.2 | | | | |
| | 110° | 72.0 | 0.7 | | | | |

TABLE 11

| | Flop index/D50 | Flop intensity $F_i$ = (Flop index · S_i)/D50 |
|---|---|---|
| Example 4 | 0.9 | 13.2 |
| Example 5 | 1.2 | 10.8 |
| Example 6 | 0.6 | 19.2 |
| Comparative example 1 | 0.7 | 5.3 |
| Comparative example 2 | 1.0 | 10.6 |
| Comparative example 3 | 1.0 | 9.5 |
| Comparative example 4 | 1.6 | 4.3 |
| Comparative example 5 | 0.5 | 3.9 |
| Comparative example 6 | 0.7 | 4.5 |
| Comparative example 7 | 0.4 | 5.4 |
| Comparative example 8 | 0.6 | 1.3 |

With the exception of Comparative example 2, the values for the flop intensity of all of the comparative examples are <10 and therefore do not have a sufficient metallic character in visual terms. In the case of Comparative example 2, the pigment in question is a metallic pigment. All of the examples possess flop intensities of >10 and therefore exhibit outstanding metallic character.

IIIc Gloss Measurements

The gloss is a measure of the directed reflection and can be characterized precisely using a Micro-Tri-Gloss instrument. More strongly scattering samples ought to exhibit a low gloss, owing to increased edge scattering and also to pigment unevennesses.

The applied coatings on black-white opacity charts were subjected to measurement using a Micro-Tri-Gloss gloss meter, from Byk Gardner, with a measurement angle of 60° relative to the vertical. The respective pigments were incorporated with stirring into a conventional nitrocellulose varnish (Or Renger Erco bronzing mixed varnish 2615e; from Morton, level of pigmentation 10% by weight, based on the total weight of the nitrocellulose varnish). The completed varnish was applied using a doctor-blade drawdown apparatus with a wet-film thickness of 76 μm to black-white opacity charts (Byko-Chart 2853, Byk-Gardner).

The gloss values listed in Table 12 below represent average values from five individual measurements in each case.

The silver-colored pigments according to the invention have a significantly stronger gloss than the comparative examples. An exception is Comparative example 5. Owing to the high transparency of this pigment, the white substrate of the opacity chart is included in the measurement.

IIId Opacity

The opacity of the pigments from the examples and comparative examples was determined on the basis of the coatings applied to black-white opacity charts from IIIc. The lightness values L* were measured with a measurement geometry of 110°, relative to the angle of emergence of the light irradiated at 45°, on the basis of these coatings applied to the black background and to the white background of the black-white opacity chart, using the Byk-mac instrument from Byk Gardner.

By formation of the opacity quotient Dq it is possible to determine measured values for the opacity of the pigments that are independent of the substrate. For this purpose, the quotient of the lightness values on the black background to the lightness values on the white background of the black-white opacity chart is calculated:

$$Dq = \frac{L^*_{110,black}}{L^*_{110,white}}$$

Where the coating systems used are identical, the opacity quotient permits a comparison of the opacity of different effect pigments with one another. The silver-colored pearlescent pigments according to the invention from Example 4 achieve an opacity comparable with that of aluminum effect pigments of the same average particle size (Comparative Example 2).

Comparative examples 3 and 4 do possess a very good opacity, but because of the very low gloss and also the high chroma values, they have no metallic effect at all and are extremely unattractive in visual terms.

TABLE 12

Opacity quotient and gloss

| | Opacity quotient 110° Byk-mac | Gloss [60°] |
|---|---|---|
| Example 4 | 0.630 | 32.1 |
| Example 5 | 0.760 | 19.6 |
| Example 6 | 0.527 | 23.0 |
| Comparative example 1 | 0.524 | 25.3 |
| Comparative example 2 | 1.001 | 19.8 |
| Comparative example 3 | 0.654 | 17.5 |
| Comparative example 4 | 0.938 | 17.4 |
| Comparative example 5 | 0.393 | 38.5 |
| Comparative example 6 | 0.515 | 18.6 |
| Comparative example 7 | 0.328 | 14.9 |
| Comparative example 8 | 0.701 | 7.0 |

IV Application-Specific Examples

The silver-colored pigments according to the invention, which were prepared according to one of the above examples, were used in the following cosmetic formulations.

Example 7

Water-in-Silicone Body Lotion

| INCI name | Product name | % by weight | Manufacturer/Supplier |
|---|---|---|---|
| Phase A | | | |
| Cyclopentasiloxane (and) Dimethiconol | Dow Corning 1501 | 11.20 | Dow Corning |
| Cyclopentasiloxane | Xiameter PMX-0245 Cyclosiloxane | 5.75 | Dow Corning |
| Cyclopentasiloxane (and) PEG/PPG-18/18 Dimethicone | Dow Corning 5225 C | 13.80 | Dow Corning |
| C 30-45 Alkyl Methicone | Dow Corning Cosmetic Wax AMS-C30 | 3.45 | Dow Corning |
| | Pigment from Example 5 | 1.00 | |
| Phase B | | | |
| Polysorbate 20 | Tween 20 | 0.60 | Croda |
| Phenoxyethanol (and) Methylparaben (and) Ethylparaben (and) Butylparaben (and) Propylparaben (and) Isobutylparaben | Uniphen P-23 | 0.35 | Induchem |
| Sodium Chloride | Sodium Chloride | 0.75 | VWR |
| Aqua | Water | 63.10 | |

The pigment from Example 5 can be used in a range from 0.2% to 2.5% by weight, based on the total weight of the body lotion formulation. The formulation can be balanced out to 100% by weight using water.

Phase A was mixed and heated to 75° C., phase B, after mixing, was heated to 70° C. and then phase B was added slowly, with homogenization, to phase A. The emulsion was cooled with stirring and was dispensed into an appropriate container.

Example 8

Eye Shadow Cream

| INCI name | Product name | % by weight | Manufacturer/Supplier |
|---|---|---|---|
| Phase A | | | |
| Castor Oil | Castor Oil | 43.70 | Honeywell Riedel-de Haen |
| Ethylhexyl Palmitate | Cegesoft C24 | 6.00 | Cognis |
| *Cocos Nucifera* (Coconut) Oil | Lipovol C-76 | 7.00 | Lipo Chemicals |
| *Cera Alba* | Ewacera 12 | 6.00 | H. Erhard Wagner |
| Isopropyl Lanolate | Ewalan IP | 5.00 | H. Erhard Wagner |
| *Persea Gratissima* (Avocado) Oil and Hydrogenated Vegetable Oil | Avocado Butter | 7.00 | Impag |

-continued

| INCI name | Product name | % by weight | Manufacturer/Supplier |
|---|---|---|---|
| Magnesium Stearate | Magnesium Stearate | 3.00 | Sigma-Aldrich |
| Bis-Hydroxyethoxypropyl Dimethicone | Dow Corning 5562 Carbinol Fluid | 7.00 | Dow Corning |
| Dimethicone/Vinyl Dimethicone Crosspolymer and Silica | Dow Corning 9701 Cosmetic Powder | 5.00 | Dow Corning |
| Phenoxyethanol (and) Methylparaben (and) Ethylparaben (and) Butylparaben (and) Propylparaben (and) Isobutylparaben | Uniphen P-23 | 0.30 | Induchem |
| Phase B | | | |
| | Pigment from Example 4 | 10.00 | |

The pigment from Example 4 can be used in a range from 5% to 22.0% by weight, based on the total weight of the eye shadow formulation. The formulation can be balanced out to 100% by weight using Castor Oil.

Phase A was mixed and heated to 85° C., and phase B was then added with stirring to phase A. The mixture is dispensed into an appropriate container and then cooled to room temperature.

Example 9

Shower Gel

| INCI name | Product name | % by weight | Manufacturer/Supplier |
|---|---|---|---|
| Phase A | | | |
| | Pigment from Example 5 | 0.50 | |
| Aqua | Water | 58.10 | |
| Acrylates Copolymer | Carbopol Aqua SF-1 | 5.50 | Lubrizol |
| Phase B | | | |
| Sodium Hydroxide | NaOH (10% by weight) | 1.50 | |
| Phase C | | | |
| Sodium Laureth Sulfate | Texapon NSO | 22.00 | Cognis |
| Cocamidopropyl Betaine | Tego Betain F 50 | 6.00 | Evonik |
| PEG-7 Glyceryl Cocoate | Emanon HE | 2.00 | Kao Corp. |
| Disodium Laureth Sulfosuccinate | Sectacin 103 Spezial | 2.00 | Zschimmmer & Schwarz |
| Phase D | | | |
| Phenoxyethanol (and) Piroctone Olamine | Nipaguard PO 5 | 0.60 | Clariant |
| Fragrance | Water Lily OA | 0.20 | Bell Flavors and Fragrances |
| Sodium Chloride | Sodium Chloride | 1.60 | VWR |

The pigment from Example 5 can be used in a range from 0.01% to 1.0% by weight, based on the total weight of the shower gel formulation. The formulation can be balanced out to 100% by weight using water.

Phase A was mixed and stirred. Then phase B was added and the mixture was stirred until it had a homogeneous appearance. Phase C was weighed out separately, mixed and added to phase AB. Stirring was then repeated and phase D was added individually.

Example 10

Pressed Eye Shadow

| INCI name | Product name | % by weight | Manufacturer/Supplier |
|---|---|---|---|
| Phase A | | | |
| Mica | Silk Mica | 17.00 | VWR |
| Boron Nitride | Softouch CCS 102 | 2.50 | Momentive |
| Zinc Stearate | Zinc Stearate | 7.00 | VWR |
| Talc | Talc Powder | 43.50 | Sigma-Aldrich |
| | Pigment from Example 6 | 20.00 | |
| Phase B | | | |
| Dimethicone | Xiameter PMX-200 Silicone Fluid 5cs | 5.00 | Dow Corning |
| Cyclopentasiloxane (and) Dimethicone Crosspolymer | Dow Corning 9040 Elastomer | 5.00 | Dow Corning |

The pigment from Example 6 can be used in a range from 5.0% to 40.0% by weight, based on the total weight of the eye shadow formulation. The formulation can be balanced out to 100% by weight using talc.

Phase A was mixed in a high-speed mixer at 2500 rpm for 30 seconds. Then phase B was added and the mixture was mixed in the same mixer at 3000 rpm for 60 seconds. Lastly the powder mixture is shaped using an eye shadow press at 150 bar for 30 seconds.

Example 11

Hair Mascara

| INCI name | Product name | % by Weight | Manufacturer/Supplier |
|---|---|---|---|
| Phase A | | | |
| Polyquaternium-16 | Luviquat FC 905 (Luviquat Exellence) | 2.70 | BASF |
| Propylene Glycol | 1,2-Propanediol | 1.80 | VWR |
| Methylparaben | Methyl-4-hydroxybenzoate | 0.20 | Sigma-Aldrich |
| Aqua | Water | 64.45 | |
| Phase B | | | |
| Cetearyl Alcohol | Lanette O | 5.00 | Cognis |
| Dimethicone | Xiameter PMX-200 Silicone Fluid 350cs | 1.00 | Dow Corning |
| Ceteareth-25 | Cremophor A 25 | 2.00 | BASF |
| Propylparaben | Propyl-4-hydroxybenzoate | 0.10 | Sigma-Aldrich |
| Phase C | | | |
| Hydroxypropylcellulose | Klucel G | 0.50 | Ashland |
| Magnesium Aluminum Silicate | Veegum HV | 0.50 | R. T. Vanderbilt |
| Aqua | Water | 19.00 | |
| Phase D | | | |
| | Pigment from Example 5 | 2.50 | |
| Phenoxyethanol (and) Methylparaben (and) Butylparaben (and) Ethylparaben (and) Propylparaben (and) Isobutylparaben | Phenonip | 0.20 | Clariant |
| Fragrance | Blue Shadow OKO | 0.05 | Bell Flavors and Fragrances |

The pigment from Example 5 can be used in a range from 1.0% to 10.0% by weight, based on the total weight of the hair mascara formulation. The formulation can be balanced out to 100% by weight using the water from phase A.

Phase A and phase B were heated separately to 80° C., and then phase B was added slowly to phase A. In a separate vessel, Klucel and Veegum were added to the water of phase C. Then phase AB was cooled to 40° C. and, in the course of cooling, phases C and D were added with stirring.

Example 12

Hair Gel

| INCI name | Product name | % by weight | Manufacturer/Supplier |
|---|---|---|---|
| Phase A | | | |
| | Pigment from Example 5 | 0.10 | |
| Ammonium Acryloyldimethyltaurate/VP Copolymer | Aristoflex AVC | 1.40 | Clariant |
| Citric Acid | Citric Acid | 0.10 | VWR |
| Aqua | Water | 55.10 | |
| Phase B | | | |
| PVP | Luviskol K 30 Powder | 1.50 | BASF |
| Propylene Glycol, Diazolidinyl, Urea, Methylparaben, Propylparaben | Germaben II | 0.20 | International Specialty Products |

-continued

| INCI name | Product name | % by weight | Manufacturer/Supplier |
|---|---|---|---|
| Triethanolamine | Triethanolamine | 1.20 | VWR |
| Water | Aqua | 40.40 | |

The pigment from Example 5 can be used in a range from 0.01% to 2.0% by weight, based on the total weight of the hair gel formulation. The formulation can be balanced out to 100% by weight using water.

The pigment from Example 5 was stirred together with water from phase A, Aristoflex AVC and Citric Acid were added with stirring, and mixing was carried out at a speed of 800 rpm for 15 minutes. Phase B was dissolved until a homogeneous solution formed, after which phase B was added to phase A and the phases were mixed.

Example 13

Body Powder

| INCI name | Product name | % by weight | Manufacturer/Supplier |
|---|---|---|---|
| Phase A | | | |
| Mica | Silk Mica | 58.70 | VWR |
| Talc | Talc Powder | 18.00 | Sigma-Aldrich |
| Boron Nitride | Softouch CCS 102 | 5.00 | Advanced Ceramics |

-continued

| INCI name | Product name | % by weight | Manufacturer/ Supplier |
|---|---|---|---|
| Nylon-12 | Orgasol 2002 D/Nat | 8.00 | Arkema |
| Magnesium Stearate | Magnesium Stearate | 6.00 | Sigma-Aldrich |
| Methylparaben, Propylparaben | Rokonsal SSH-1 | 0.30 | ISP Biochema |
|  | Pigment from Example 4 | 2.00 |  |
| Phase B |  |  |  |
| Tridecyl Stearate (and) Tridecyl Trimellitate (and) Dipentaerythrityl Hexacaprylate/Hexaeaprate | Lipovol MOS-130 | 2.00 | Lipo Chemicals |

The pigment from Example 4 can be used in a range from 0.2% to 5.0% by weight, based on the total weight of the body powder formulation. The formulation can be balanced out to 100% by weight using Silk Mica.

Phase A was mixed, then phase B was added to phase A and the body powder was dispensed into a suitable vessel.

Example 14

Lip Gloss

| INCI name | Product name | % by weight | Manufacturer/ Supplier |
|---|---|---|---|
| Phase A |  |  |  |
| Hydrogenated Polyisobutene (and) Ethylene/Propylene/ Styrene Copolymer (and) Butylene/Ethylene/Styrene Copolymer | Versagel ME 750 | 79.00 | Calumet Penreco |
| Simmondsia Chinensis (Jojoba) Seed Oil | Jojoba Oil - Natural/Golden | 2.00 | BioChemica |
| Caprylyl Trimethicone | Silcare Silicone 31M50 | 7.00 | Clariant |
| Stearyl Dimethicone | Silcare Silicone 41M65 | 3.20 | Clariant |
| Hydrogenated Polydecene | Nexbase 2002 | 4.00 | Jan Dekker |
| Isopropyl Myristate | Isopropyl Myristate | 4.50 | VWR |
| Phase B |  |  |  |
|  | Pigment from Example 5 | 0.10 |  |
| Propylparaben | Propyl-4-hydroxy-benzoate | 0.20 | Sigma-Aldrich |

The pigment from Example 5 can be used in a range from 0.10% to 8.00% by weight, based on the total weight of the lip gloss formulation. The formulation can be balanced out to 100% by weight using Versagel ME 750.

Phase A was heated to 85° C., and then the ingredients of phase B were added individually to phase A, and the composition was stirred until its consistency was uniform, after which it was dispensed into a lip gloss vessel.

Example 15

Lip Contour Pencil

| INCI name | Product name | % by weight | Manufacturer/ Supplier |
|---|---|---|---|
| Phase A |  |  |  |
| Hydrogenated Coco-Glycerides | Softisan 100 | 12.35 | Sasol Wax |
| Candelilla Cera | Ewacera 42 | 14.00 | H. Erhard Wagner |
| Magnesium Stearate | Magnesium Stearate | 6.00 | Sigma-Aldrich |
| Stearic Acid | Kortacid 1895 | 8.50 | Akzo Nobel |
| Hydrogenated Coconut Oil | Lipex 401 | 8.00 | Aarhus Karlshamn |
| Cetyl Palmitate | Kahlwax 7157 | 7.00 | Kahl |
| Caprylic/Capric Triglyceride | Liponate GC-K | 3.60 | Lipo Chemicals |
| Soybean Glycerides (and) Butyrospermum Parkii | Lipex L'sens | 15.00 | Aarhus Karlshamn |
| Tocopheryl Acetate | di-alpha-Tocopheryl Acetate | 0.25 | Jan Dekker |
| Methylparaben; Propylparaben | Rokonsal SSH-1 | 0.30 | ISP Biochema |
| Phase B |  |  |  |
|  | Pigment from Example 6 | 25.00 |  |

The pigment from Example 6 can be used in a range from 15% to 25% by weight, based on the total weight of the lip contour pencil formulation. Alternatively, in addition to the pigment from Example 6, it is possible to add further color pigments and/or effect pigments, although the maximum level of pigmentation of 25% by weight pigment ought not to be exceeded.

Phase A was heated to 85° C. and then phase B was added to phase A with stirring until the composition was uniform. Thereafter the mixture was introduced while hot into a pencil mold.

Example 16

Lipstick

| INCI name | Product name | % by weight | Manufacturer/ Supplier |
|---|---|---|---|
| Phase A |  |  |  |
| Carnauba Wax | Ewacera 34 | 4.50 | H. Erhard Wagner |
| Cera Alba | Ewacera 12 | 3.50 | H. Erhard Wagner |
| Candelilla Cera Extract | Ewacera 42 | 4.00 | H. Erhard Wagner |
| Microcrystalline Wax | TeCero-Wax 1030 K | 7.20 | TH.C. Tromm |
| Cetyl Palmitate | Kahlwax 7157 | 2.00 | Kahl |
| Hydrogenated Coco-Glycerides | Softisan 100 | 5.00 | Sasol Wax |
| Petrolatum | Penreco Blond | 5.80 | Calumet Penreco |
| Cetearyl Ethylhexanoate | Luvitol EHO | 10.70 | BASF |
| Tocopheryl Acetate | di-alpha-Tocopheryl Acetate | 0.50 | Jan Dekker |

| INCI name | Product name | % by weight | Manufacturer/Supplier |
|---|---|---|---|
| Castor Oil | Castor Oil | 46.60 | Honeywell Riedel-de Haan |
| Phase B | | | |
| | Pigment from Example 4 | 10.00 | |
| Methylparaben, Propylparaben | Rokonsal SSH-1 | 0.20 | ISP Biochema |

The pigment from Example 4 can be used in a range from 0.5% to 21.0% by weight, based on the total weight of the lipstick formulation. The formulation can be balanced out to 100% by weight using castor oil.

Phase A was heated to 85° C., and then phase B was added to phase A and the phases were mixed. This mixture was subsequently dispensed at a temperature of 75° C. in a lipstick mold.

Example 17

Liquid Eye Liner

| INCI name | Product name | % by weight | Manufacturer/Supplier |
|---|---|---|---|
| Phase A | | | |
| Aqua | Water | 66.70 | |
| Water/carbon black dispersion | MBD 201 | 3.00 | Geotech |
| Acrylates Copolymer | Covacryl E14 | 10.00 | LCW |
| Magnesium Aluminum Silicate | Veegum HV | 1.00 | C. H. Erbsioh |
| Phase B | | | |
| Propylene Glycol | 1,2-Propanediol | 3.00 | VWR |
| Triethanolamine | Triethanolamine | 1.40 | VWR |
| Phase C | | | |
| Xanthan Gum | Keltrol CG-T | 0.30 | CP Kelco |
| Phase D | | | |
| | Pigment from Example 6 | 3.00 | |
| Mica | Silk Mica | 2.00 | VWR |
| Phase E | | | |
| Stearic Acid | Kortacid 1895 | 2.80 | Akzo Nobel |
| Glyceryl Stearate | Aldo MS K FG | 0.80 | Lonza |
| Oleyl Alcohol | HD-Ocenol 90/95 V | 0.50 | Cognis |
| Phenoxyethanol (and) Methylparaben (and) Ethylparaben (and) Butylparaben (and) Propylparaben (and) Isobutylparaben | Uniphen P-23 | 0.50 | Induchem |
| Phase F | | | |
| Dimethicone (and) Trisiloxane | Xiameter PMX-1184 Silicone Fluid | 5.00 | Dow Corning |

The pigment from Example 6 can be used in a range from 0.5% to 8.0% by weight, based on the total weight of the eye liner formulation. The formulation can be balanced out to 100% by weight using water.

Veegum was dispersed in phase A and stirred for 15 minutes, after which phase B was added to phase A, and then phase C to phase AB, followed by stirring again for 10 minutes. Then phase D was added to phase ABC and the mixture was heated to 75° C., and phase E was likewise heated to 75° C. and then added to phase ABCD. After cooling to 60° C. had taken place, phase F was added, and the mixture was dispensed into a suitable vessel.

Example 18

Mousse

| INCI name | Product name | % by weight | Manufacturer/Supplier |
|---|---|---|---|
| Phase A | | | |
| Cyclopentasiloxane | Xiameter PMX-0245 Cyclosiloxane | 8.60 | Dow Corning |
| Hydrogenated Polyisobutene | MC 30 | 4.00 | Sophim |
| Dimethicone (and) Dimethicone Crosspolymer | Dow Corning 9041 Silicone Elastomer Blend | 37.14 | Dow Corning |
| Squalane | Squalane | 5.74 | Impag |
| Isononyl Isononanoate | Dermal 99 | 10.16 | Akzo International |
| Hydrogenated Jojoba Oil | Jojoba Butter LM | 2.15 | Desert Whale |
| Hydrogenated Jojoba Oil | Jojoba Butter HM | 1.00 | Desert Whale |

-continued

| INCI name | Product name | % by weight | Manufacturer/Supplier |
|---|---|---|---|
| C30-45 Alkyl Methicone (and) C30-45 Olefin | Dow Corning AMS-C30 Cosmetic Wax | 1.15 | Dow Corning |
| Stearyl Dimethicone | Dow Corning 2503 Cosmetic Wax | 0.47 | Dow Corning |

-continued

| INCI name | Product name | % by weight | Manufacturer/Supplier |
|---|---|---|---|
| Cyclopentasiloxane (and) Polypropylsilsesquioxane | Dow Corning 670 Fluid | 5.00 | Dow Corning |
| Phase B | | | |
| Dimethicone/Vinyl Dimethicone Crosspolymer | Dow Corning 9506 Powder | 16.02 | Dow Corning |
| Silica Dimethyl Silylate | Covasilic 15 | 0.17 | LCW |
| Talc | Talc Powder | 5.00 | Sigma-Aldrich |
| | Pigment from Example 4 | 3.00 | |
| Phase D | | | |
| Propylene Glycol, Diazolidinyl Urea, Methylparaben, Propylparaben | Germaben II | 0.40 | International Speciality Products |

The pigment from Example 4 can be used in a range from 0.1% to 8.0% by weight, based on the total weight of the mousse formulation. The formulation can be balanced out to 100% by weight using Dow Corning 9041 elastomer.

Phase A was mixed and heated until everything had melted. Phase B was weighed out separately and mixed with a high-speed mixer at 2400 rpm for 60 seconds. Half of the melted phase A was added to phase B, and mixing was repeated in the mixer at 2400 rpm for 30 seconds. Then the remainder of phase B was likewise added to phase A, followed again by mixing at 2400 rpm for 30 seconds. Lastly, phase C is added to phase AB and mixing is repeated at 2400 rpm for 30 seconds in the high-speed mixer.

Example 19

Nail Varnish

| INCI name | Product name | % by weight | Manufacturer/Supplier |
|---|---|---|---|
| Phase A | | | |
| | Pigment from Example 4 | 2.00 | |
| Phase B | | | |
| Butyl acetate (and) Ethyl acetate (and) Nitrocellulose (and) Isopropyl Alcohol | International Lacquers Nailpolish & Care Base 359 | 98.00 | International Lacquers |

The pigment from Example 4 can be used in a range from 0.1% to 10.0% by weight, based on the total weight of the nail varnish formulation. The formulation can be balanced out to 100% by weight using International Lacquers Nailpolish.

Phase A and phase B were mixed and then dispensed into an appropriate container.

Example 20

Nail Varnish with Soft Touch Effect

| INCI name | Product name | % by weight | Manufacturer/Supplier |
|---|---|---|---|
| Phase A | | | |
| | Pigment from Example 4 | 2.00 | |
| | Ceraflour 913 | 5.00 | Byk Chemie |
| Phase B | | | |
| Butyl acetate (and) Ethyl acetate (and) Nitrocellulose (and) Isopropyl Alcohol | International Lacquers Nailpolish & Care Base 359 | 93.00 | International Lacquers |

The pigment from Example 4 can be used in a range from 0.1% to 10.0% by weight, based on the total weight of the nail varnish formulation. The formulation can be balanced out to 100% by weight using international Lacquers Nailpolish.

Phase A was mixed, added to phase B, and then the nail varnish was dispensed into an appropriate container.

Example 21

Aqueous Nail Varnish

The pigments from Examples 4 to 6 can be used in an aqueous nail varnish according to WO 2007/115675 A2 Example 1. The level of pigmentation in this case is 0.1% to 10.0% by weight, based on the total weight of the formulation.

Example 22

Liquid Eye Shadow

| INCI name | Product name | % by weight | Manufacturer/Supplier |
|---|---|---|---|
| Phase A | | | |
| Water | Aqua | 70.10 | |
| Glycerin | Pricerine 9090 | 6.00 | Croda |
| Phase B | | | |
| PEG-800 | Polyglycol 35000 S | 0.60 | Clariant |
| Allantoin | Allantoin | 0.30 | 3 V |
| Ammonium Acryloyldimethyltaurate/VP Copolymer | Aristoflex AVC | 0.80 | Clariant |
| Acrylates Copolymer | Worlee Micromer CEK 20/50 | 5.00 | Worlee |
| Phase C | | | |
| | Pigment from Example 6 | 10.00 | |
| Divinyldimethicone/Dimethicone Copolymer | Dow Corning HMW 2220 Non-ionic Emulsion | 6.00 | Dow Corning |
| C12-C13 Pareth-3, C12-C13 Pareth-23 | | | |

-continued

| INCI name | Product name | % by weight | Manufacturer/ Supplier |
|---|---|---|---|
| Fragrance | Water Lily OA | 0.20 | Bell Flavors and Fragrances |
| Phenoxyethanol (and) Methylparaben (and) Butylparaben (and) Ethylparaben (and) Propylparaben (and) Isobutylparaben | Phenonip | 1.00 | Clariant |

The pigment from Example 6 can be used in a range from 0.10% to 17.00% by weight, based on the total weight of the eye shadow formulation. The formulation can be balanced out to 100% by weight using water.

Phase A was stirred, and then the ingredients of phase B were added individually to phase A and the mixture was stirred until its consistency was uniform. Thereafter the ingredients of phase C were added individually to phase AB and the mixture was stirred until its consistency was uniform again.

What is claimed is:

1. A silver-colored pigment having a metallic character or effect and comprising a nonmetallic platelet-shaped substrate, at least one titanium oxide layer, and at least one ilmenite-containing coating,
    wherein the nonmetallic platelet-shaped substrate is a nonmetallic platelet-shaped synthetic substrate and the amount of iron compounds, calculated as elemental iron, in the pigment is less than 5.0% by weight, based on the total weight of the pigment,
    wherein the at least one ilmenite-containing coating has a concentration gradient which decreases in the substrate direction, and
    wherein the pigment has a flop intensity $F_i$, defined as the product of flop index and glitter intensity $S\_i$ as a function of the average particle size $D_{50}$, in accordance with formula (II)

$$\text{Flop intensity }(F_i) = \frac{\text{Flop index} \cdot S\_i}{D_{50}}, \quad (II)$$

of at least 10.

2. The silver-colored pigment according to claim 1, wherein the pigment comprises the following structure:
    (a) nonmetallic platelet-shaped synthetic substrate,
    (b) titanium oxide layer, and
    (c) ilmenite layer.

3. The silver-colored pigment according to claim 1, wherein the pigment has an iron(III) oxide content of less than 0.5% by weight, based on the total weight of the pigment.

4. The silver-colored pigment according to claim 1, wherein the silver-colored pigment has a chroma with a measurement geometry of 110°, relative to the angle of emergence of the light irradiated at 45°, is $C^*_{110} \leq 2.4$.

5. The silver-colored pigment according to claim 1, wherein the ilmenite-containing coating layer of the pigment has an average layer thickness from a range from 1 nm to 20 nm.

6. The silver-colored pigment according to claim 1, wherein the pigment has an iron/titanium weight ratio as a function of the coating, in accordance with formula (I)

$$\frac{\text{Iron content (\% by weight)}}{\text{Titanium content (\% by weight)}} \quad (I)$$

Fraction of the coating (% by weight), in a range from 1 to 8,
    where "iron content" stands for the amount of iron compounds, calculated as elemental iron, and "titanium content" stands for the amount of titanium compounds, calculated as elemental titanium, in each case in the pigment and based on the total weight of the pigment, and where the "fraction of the coating (% by weight)" stands for the weight fraction, based on the total weight of the pigment, of the coating applied to the substrate.

7. The silver-colored pigment according to claim 1, wherein the nonmetallic platelet-shaped synthetic substrate is selected from the group consisting of synthetic mica platelets, glass platelets, $SiO_2$ platelets, $Al_2O_3$ latelets, synthetic boehmite platelets, polymer platelets, synthetic platelet-shaped substrates which comprise an inorganic-organic hybrid layer, and mixtures thereof.

8. The silver-colored pigment according to claim 7, wherein the nonmetallic platelet-shaped substrate consists of synthetic mica.

9. The silver-colored pigment according to claim 1, wherein the pigment contains a titanium dioxide layer in rutile form.

10. The silver-colored pigment according to claim 2, wherein the fraction of titanium oxide in the coating decreases from the substrate-facing side to the substrate-remote side of the titanium oxide layer.

11. A process for preparing silver-colored pigment comprising:
    (i) applying an uncalcined titanium oxide/titanium hydroxide/titanium oxide hydrate layer to a nonmetallic, platelet-shaped, synthetic substrate,
    (ii) applying an iron oxide/iron hydroxide/iron oxide hydrate layer to the uncalcined titanium oxide/titanium hydroxide/titanium oxide hydrate layer, and
    (iii) calcining the product obtained in step (ii), under reducing conditions,
    wherein the silver-colored pigment, has a metallic character or effect and comprises a nonmetallic platelet-shaped substrate, at least one titanium oxide layer ,and at least one ilmenite-containing coating,
    wherein the nonmetallic platelet-shaped substrate is a nonmetallic platelet-shaped synthetic substrate and the amount of iron compounds, calculated as elemental iron, in the pigment is less than 5.0% by weight, based on the total weight of the pigment,
    wherein the at least one ilmenite-containing, coating has a concentration gradient which decreases in the substrate direction, and
    wherein the pigment has a flop intensity $F_i$, defined as the product of flop index and glitter itensity $S\_i$ as function of the average particle size $D_{50}$,in accordance with formula (II)

$$\text{Flop intensity }(F_i) = \frac{\text{Flop index} \cdot S\_i}{D_{50}}, \quad (II)$$

of at least 10.

12. A process for producing a pigmented cosmetic formulation, plastic, film, textile, ceramic material, glass or coating composition, comprising introducing the silver-colored pigment of claim 1 into a cosmetic formulation, plastic, film, textile, ceramic material, glass or coating composition.

13. A preparation comprising the silver-colored pigment according to claim 1.

14. An object comprising the silver-colored pigment according to claim 1.

15. The process according to claim 12, wherein the coating composition is selected from the group consisting of varnish, ink, printer ink, paint, and powder coating material.

16. The preparation according to claim 13, wherein the preparation is a coating composition, cosmetic formulation or plastic.

17. The preparation according to claim 16, wherein the coating composition is selected from the group consisting of varnish, ink, printer ink, paint, and powder coating material.

18. The silver-colored pigment according to claim 1, wherein the pigment further comprises at least one external protective layer.

19. The silver-colored pigment according to claim 18, wherein the external protective layer comprises at least one layer selected from the group consisting of metal oxide layer, metal hydroxide layer, metal oxide hydrate layer and combinations thereof.

20. The silver-colored pigment according to claim 19, wherein each of the metal oxide layer, metal hydroxide layer, and metal oxide hydrate layer comprises an element independently selected from the group consisting of Si, Al, Zr and Ce.

21. The silver-colored pigment according to claim 19, wherein the external protective layer has one or more silanes applied to a surface thereof.

22. The silver-colored pigment according to claim 19, wherein the external protective layer has one or more organic-chemical modifying agents applied to a surface thereof.

23. The silver-colored pigment according to claim 22, wherein the organic-chemical modifying agent is selected from the group consisting of substituted or unsubstituted alkyl radicals, polyethers, thioethers, siloxanes and mixtures thereof.

24. The silver-colored pigment according to claim 22, wherein the organic-chemical modifying agent contains at least one reactive chemical group selected from the group consisting of acrylate, methacrylate, vinyl, isocyanate, cyano, epoxy, hydroxy, amino and mixtures thereof.

25. The silver-colored pigment according to claim 19, wherein the external protective layer has one or more inorganic-chemical modifying agents applied to a surface thereof.

26. The silver-colored pigment according to claim 25, wherein inorganic-chemical modifying agent is selected from the group consisting of $Al_2O_3$, $ZrO_2$ and mixtures thereof.

27. The silver-colored pigment according to claim 2, wherein the pigment is obtained by
   (i) applying an uncalcined titanium oxide/titanium hydroxide/titanium oxide hydrate layer to a nonmetallic, platelet-shaped, synthetic substrate,
   (ii) applying an iron oxide/iron hydroxide/iron oxide hydrate layer to the uncalcined titanium oxide/titanium hydroxide/titanium oxide hydrate layer,
   (iii) calcining the product obtained in step (ii), under reducing conditions.

\* \* \* \* \*

UNITED STATES PATENT AND TRADEMARK OFFICE
CERTIFICATE OF CORRECTION

PATENT NO. : 9,265,701 B2  
APPLICATION NO. : 14/007285  
DATED : February 23, 2016  
INVENTOR(S) : Michael Grüner et al.

Page 1 of 1

It is certified that error appears in the above-identified patent and that said Letters Patent is hereby corrected as shown below:

Claims

Column 46, Line 19, Claim 7, delete "latelets," and insert -- platelets, --

Column 46, Line 46, Claim 11, delete "layer ,and" and insert -- layer, and --

Column 46, Line 53, Claim 11, after "ilmenite-containing" delete ","

Column 46, Line 58, Claim 11, delete "itensity" and insert -- intensity --

Column 46, Line 58, Claim 11, delete "$D_{50}$,in" and insert -- $D_{50}$, in --

Signed and Sealed this
Nineteenth Day of July, 2016

Michelle K. Lee
*Director of the United States Patent and Trademark Office*